US008343929B2

(12) United States Patent
Shaari

(10) Patent No.: US 8,343,929 B2
(45) Date of Patent: *Jan. 1, 2013

(54) TREATING NEOPLASMS WITH NEUROTOXIN

(75) Inventor: Christopher Shaari, Demarest, NJ (US)

(73) Assignee: Toxcure, Inc., Demarest, NJ (US)

( * ) Notice: Subject to any disclaimer, the term of this patent is extended or adjusted under 35 U.S.C. 154(b) by 374 days.

This patent is subject to a terminal disclaimer.

(21) Appl. No.: 12/592,540

(22) Filed: Nov. 25, 2009

(65) Prior Publication Data

US 2010/0172939 A1 Jul. 8, 2010

Related U.S. Application Data

(63) Continuation-in-part of application No. 11/577,838, filed as application No. PCT/US2005/033982 on Sep. 23, 2005, now Pat. No. 7,709,440.

(60) Provisional application No. 60/612,443, filed on Sep. 23, 2004, provisional application No. 61/118,036, filed on Nov. 26, 2008.

(51) Int. Cl.
A61K 38/00 (2006.01)

(52) U.S. Cl. ...................................... 514/19.3; 530/350
(58) Field of Classification Search ........................ None
See application file for complete search history.

(56) References Cited

U.S. PATENT DOCUMENTS

| 5,766,605 | A | 6/1998 | Sanders et al. |
| 6,139,845 | A | 10/2000 | Donovan |
| 6,565,870 | B1 | 5/2003 | Donovan |
| 2001/0021695 | A1 | 9/2001 | Aoki et al. |
| 2002/0094339 | A1 | 7/2002 | Donovan |
| 2005/0031648 | A1* | 2/2005 | Brin et al. .................. 424/239.1 |
| 2006/0286127 | A1 | 12/2006 | Van Schaack et al. |

FOREIGN PATENT DOCUMENTS

| EP | 1 599 218 | 11/2005 |
| EP | 1 604 678 | 12/2005 |
| EP | 1 804 827 | 7/2007 |
| EP | 1 890 714 | 2/2008 |
| EP | 1 990 059 | 11/2008 |
| WO | WO 01/78760 | 10/2001 |
| WO | WO 01/82961 | 11/2001 |
| WO | WO 02/07759 | 1/2002 |
| WO | WO 02/09743 | 2/2002 |
| WO | WO 2004/071525 | 8/2004 |
| WO | WO 2004/076634 | 9/2004 |
| WO | WO 2004/078202 | 9/2004 |
| WO | WO 2004/112830 | 12/2004 |
| WO | WO 2005/030248 | 4/2005 |
| WO | WO 2005/056050 | 6/2005 |
| WO | WO 2006/025976 | 3/2006 |
| WO | WO 2006/094539 | 9/2006 |
| WO | WO 2006/138059 | 12/2006 |

OTHER PUBLICATIONS

Ansiaux, R. et al., "Botulinum Toxin Potentiates Cancer Radiotherapy and Chemotherapy," Clin Cancer Res 12(4): pp. 1276-1283 (2006).
Ansiaux, R. et al., "Use of Botulinum Toxins in Cancer Therapy," Expert Opinion on Investigational Drugs 16(2): pp. 209-218 (2007).
Black, et al. Cell Biol. 103(2): pp. 535-544 (1986).
Childers M. K., et al. "Comparison of Two Injection Technique Using Botulinum Toxin in Spastic Hemiplegia," American Journal of Physical Medicine & Rehabilitation/Association of Academic Physiatrists. 75(6): pp. 462-469 (1996).
Cron G 0 et al. "Botulinum Toxin Increases Tumor uptake of Gemcitabine Chemotherapy as Measured with Fluorine Spectroscopy" Proceedings of the International Society for Magnetic Resonance in Medicine, vol. 16 p. 1764 (2006).
European Patent Office Communication mailed Sep. 2, 2009 in European Application No. 05 814 023.
European Search Report completed on Feb. 12, 2010 for European Application No. 10000417.
European Search Report completed on Feb. 10, 2011 for European Application No. 10012869.
Gura, Science, 1997, 278:1041-1042.
Hesse, et al. Neurosci Lett. 201(1): pp. 37-40 (1995).
Hesse, et al. Clin Rehabli 12(5): p. 3810388 (1998).
Hiroto, M. et al., Journal of Pancreas 6(2): pp. 143-151 (2005).
International Search Report mated on Jun. 12, 2006 for International Application No. PCT/US05/33982.
International Search Report maied on Mar. 22, 2010 for International Application No. PCT/US09/65919.
Lang et al, Methods in Ezymology, 2005, 1995, 256:320-327.
Noguera, et al. "Botulinum Toxin in the Treatment of Spasticity in HIV-infected Children Affected with Progressive Encephalopathy," AIDS 18(2): (2004) see e.g. pp. 352-353.
Qiu, Y. H Peng, Y. P., et al. "Effect of acetylcholine on in vitro IL-2 production and NK cell cytotoxicity of rats," Lymphology 37(1): pp. 31-38 (2004).
Shaari and Sanders, Quantifying How Location and Dose of Botulinurn Toxin Injections Affect Muscle Paralysis, Muscle and Nerve, 1993, vol. 16, pp. 964-969.

(Continued)

*Primary Examiner* — Misook Yu
*Assistant Examiner* — Mark Halvorson
(74) *Attorney, Agent, or Firm* — Frommer Lawrence & Haug, LLP

(57) ABSTRACT

The present invention provides a method of treating a neoplasm using a neurotoxin, preferably botulinum toxin. Neurotoxin administered around a neoplasm acts to decrease the contractile forces of the muscles surrounding a neoplasm which normally squeeze neoplastic cells through efferent channels leaving the neoplasm to distant sites. The present invention also provides a method of administering botulinum toxin at sites distant from the neoplasm, thereby enhancing cellular and humoral immunologic functions, which further contribute to neoplastic cell death. Following administration of botulinum toxin around or distant to a neoplasm as described herein, local, regional, and distant spread of neoplastic cells is reduced or eliminated. Immunomodulation with botulinum toxin is also valuable in treating other diseases that may or may not be associated with cancers, such as viral-induced growths, viral conditions, fungal disease, chronic wounds, graft versus host disease, autoimmune disease, and HIV.

9 Claims, 2 Drawing Sheets

OTHER PUBLICATIONS

Shaari, et al., Botulinum Toxin Decreases Salivation from Canine Submandibular Glands, Otolaryngology-Head and Neck Surgery, 1998, vol. 118, pp. 452-457.

Shaari, et al. Rhinorrhea is decreased in Dogs After the Nasal Application of Botulinum Toxin, Otolaryngology-Head and Neck Surgery, 1995, vol. 112, pp. 566-571.

Shaari, et al., Quantifying the Spread of Botulinum Toxin Through Muscle Fascia, Laryngoscope, 1991, vol. 101, pp. 960-964.

Shaari, et al., Study of Botulinum Toxin Injection Parameters, Report of Defense of Dissertation M.D. with Distinction in Research Albany medical College Archives, Mar. 11, 1991.

Shaari and Sanders, The Assessment of Biologic Activity of Botulinum Toxin, In: Jankovic J. Hallett M, eds. Therapy with Botulinum Toxin, New York, New York, Marcel Dekker, Inc., 1994, pp. 159-170.

Shantz, E. J., et al., "Properties and Use of Botulinum Toxin and Other Microbial Neurotoxins in Medicine," Microbiol Rev. 56: pp. 80-99 (1992).

Supplemental European Search Report mailed on Jan. 28,2008 for European Application No. EP 5 814 023.

Tang-Liu, et al. "Intramuscular Injection of $^{125}$I-botulinum Neurotoxin-Complex Versus $^{125}$I-botulinum-free Neurotoxin: Time Course of Tissue Distribution," Toxicon 42: pp. 461-469 (2003).

Targarona, E. M., et al., World J Surg 22, pp. 57-58 (1998).

Valitutti et al, J Exp Med. 1995, 181:577-584.

Whiteside, T. L., Allergy Clin Immunol 111: pp. S677-S686 (2003).

Woodside et al, J Exp Med, 1998, 188:1211-1221.

\* cited by examiner

Figure 1    Growth of the human colorectal tumour xenograft, HCT116, following treatment with Botulinum Toxin A, Paclitaxel, Botulinum Toxin A + Paclitaxel or the corresponding vehicle groups

DMSO in 5 % ethanol, 10 % cremaphor, 85 % sterile saline (0.9 % w/v).
* 0.9 % w/v sterile saline.
n=10 unless otherwise stated in parenthesis Figure 2    Individual tumour growth modelling of the human colorectal tumour xenograft, HCT116, following treatment with Botulinum Toxin A, Paclitaxel, Botulinum Toxin A + Paclitaxel or corresponding vehicle groups Natural logarithmic transformation of individual animals relative tumour volume ($V/V_0$) expressed in terms of a linear regression with intercept of 0.

TREATING NEOPLASMS WITH NEUROTOXIN

INCORPORATION BY REFERENCE

This application is a continuation-in-part application of U.S. patent application Ser. No. 11/577,838 filed Apr. 24, 2007, which is the national stage of International Application No. PCT/US05/33982, filed Sep. 23, 2005, which claims the benefit of priority of U.S. provisional application Ser. No. 60/612,443, filed Sep. 23, 2004, and this application claims the benefit of priority of U.S. provisional application Ser. No. 61/118,036, filed Nov. 26, 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to methods for treating various neoplasms, chronic infections, autoimmune diseases, and immunodeficiencies. In particular, the present invention relates to methods of treating the growth and metastasis of various neoplasms with a botulinum toxin, either alone or in combination with an anti-cancer drug.

BACKGROUND OF THE INVENTION

A neoplasm is an abnormal mass of tissue resulting from the abnormal proliferation of cells. The growth of a neoplasm exceeds and is uncoordinated with that of the normal (i.e., non-neoplastic) tissues around it. Neoplasms typically cause a lump or a tumor and may be benign, pre-malignant, or malignant. The initial growth of a neoplasm is dependent upon adequate supply of growth factors and the removal of toxic molecules. The expansion of tumor mass beyond 2 mm in diameter depends on the development of angiogenesis to produce adequate blood supply. The induction of angiogenesis is mediated by multiple molecules that are released by both tumor cells and host cells, including endothelial cells, epithelial cells, mesothelial cells, and leukocytes. Angiogenesis comprises sequential processes emanating from microvascular endothelial cells. As it expands, the tumor (primary or secondary) can also cause certain symptoms, such as discomfort (e.g., the feeling of a lump), pain and bleeding. After angiogenesis begins, tumor cell invasion of the tissue surrounding the primary tumor and penetration of blood and lymph vessels is central to the whole phenomenon of metastasis.

Once tumor cells detach from the primary tumor, they must invade the host stroma to penetrate lymphatics and blood vessels. To do so, tumor cells must penetrate basement membranes surrounding blood vessels. Basement membranes and connective tissue extracellular matrix (ECM) is comprised of four major groups of molecules: collagens, elastins, glycoproteins, and proteoglycans. The degradation of the ECM and basement membrane components by tumor cells is an important prerequisite for invasion and metastasis.

Cancer metastasis is comprised of multiple complex, interacting, and interdependent steps, each of which is rate-limiting, since a failure to complete any of the steps prevents the tumor cell from producing a metastasis. The tumor cells that eventually give rise to metastases must survive a series of potentially lethal interactions with host homeostatic mechanisms. The balance of these interactions can vary among different patients with different neoplasms or even among different patients with the same type of neoplasm.

The important steps in the formation of a metastasis are similar in all tumors and comprises the following:

1. After neoplastic transformation, progressive proliferation of neoplastic cells is initially supported with nutrients supplied from the organ microenvironment by diffusion.
2. Neovascularization or angiogenesis must take place for a tumor mass to exceed 1 or 2 mm in diameter. The synthesis and secretion of different angiogenic molecules and suppression of inhibitory molecules are responsible for the establishment of a capillary network from the surrounding host tissue.
3. Some tumor cells can down regulate expression of cohesive molecules and have increased motility, thus can detach from the primary lesion. Invasion of the host stroma by some tumor cells occurs by several parallel mechanisms. Capillaries and thin-walled venules, like lymphatic channels, offer very little resistance to penetration by tumor cells and provide the most common pathways for tumor cell entry into the circulation.
4. Detachment and embolization of single tumor cells or cell aggregates occur next, the vast majority of circulating tumor cells being rapidly destroyed.
5. Once the tumor cells have survived circulation, they must arrest in the capillary beds of distant organs by adhering either to capillary endothelial cells or to exposed subendothelial basement membranes.
6. Tumor cells (especially those in aggregates) can proliferate within the lumen of the blood vessel, but the majority move into the organ parenchyma by mechanisms similar to those operative during invasion.
7. Tumor cells bearing appropriate cell surface receptors respond to paracrine growth factors and hence proliferate in the organ parenchyma.
8. The metastatic cells must evade destruction by host defenses that include specific and nonspecific immune responses.
9. To exceed a mass of 1 to 2 mm in diameter, metastasis must develop a vascular network.

There are several chemotherapy drugs and anti-cancer therapies currently used to treat a variety of cancers by, for example, damaging DNA in the cancer cell to preventing the cell from reproducing. Chemotherapy drugs can be divided into several groups based on factors such as how they work, their chemical structure, and their relationship to another drug. Because some drugs act in more than one way, they may belong to more than one group.

Alkylating agents directly damage DNA to prevent the cancer cell from reproducing. As a class of drugs, these agents are not phase-specific; in other words, they work in all phases of the cell cycle. Alkylating agents are used to treat many different cancers, including acute and chronic leukemia, lymphoma, Hodgkin disease, multiple myeloma, sarcoma, as well as cancers of the lung, breast, and ovary. Because these drugs damage DNA, they can cause long-term damage to the bone marrow. In a few rare cases, this can eventually lead to acute leukemia. The risk of leukemia from alkylating agents is "dose-dependent," meaning that the risk is small with lower doses, but goes up as the total amount of drug used gets higher. The risk of leukemia after alkylating agents is highest 5 to 10 years after treatment. There are many different alkylating agents, including: nitrogen mustards, such as mechlorethamine (nitrogen mustard), chlorambucil, cyclophosphamide (Cytoxan®), ifosfamide, and melphalan; nitrosoureas, such as streptozocin, carmustine (BCNU), and lomustine; alkyl sulfonates, which include busulfan; triazines, such as dacarbazine (DTIC), and temozolomide (Temodar®); and ethylenimines such as thiotepa and altretamine (hexamethylmelamine). The platinum drugs (cisplatin, carboplatin, and oxalaplatin) are sometimes grouped with alkylating agents because they kill cells in a similar way. These drugs are less likely than the alkylating agents to cause leukemia.

Antimetabolites are a class of drugs that interfere with DNA and RNA growth by substituting for the normal building blocks of RNA and DNA. These agents damage cells during the S phase. They are commonly used to treat leukemias, tumors of the breast, ovary, and the intestinal tract, as well as other cancers. Examples of antimetabolites include 5-fluorouracil (5-FU), capecitabine (Xeloda®), 6-mercaptopurine (6-MP), methotrexate, gemcitabine (Gemzar®), cytarabine (Ara-C®), fludarabine, and pemetrexed (Alimta®).

Anthracyclines are anti-tumor antibiotics that interfere with enzymes involved in DNA replication. These agents work in all phases of the cell cycle. Thus, they are widely used for a variety of cancers. A major consideration when giving these drugs is that they can permanently damage the heart if given in high doses. For this reason, lifetime dose limits are often placed on these drugs. Examples of anthracyclines include daunorubicin, doxorubicin (Adriamycin®), epirubicin, and idarubicin. Other anti-tumor antibiotics include the drugs actinomycin-D, bleomycin, and mitomycin-C.

Mitoxantrone is an anti-tumor antibiotic that is similar to doxorubicin in many ways, including the potential for damaging the heart. This drug also acts as a topoisomerase II inhibitor, and can lead to treatment-related leukemia. Mitoxantrone is used to treat prostate cancer, breast cancer, lymphoma, and leukemia.

Topoisomerase inhibitors interfere with enzymes called topoisomerases, which help separate the strands of DNA so they can be copied. They are used to treat certain leukemias, as well as lung, ovarian, gastrointestinal, and other cancers. Examples of topoisomerase I inhibitors include topotecan and irinotecan (CPT-11). Examples of topoisomerase II inhibitors include etoposide (VP-16) and teniposide. Treatment with topoisomerase II inhibitors increases the risk of a second cancer—acute myelogenous leukemia. Secondary leukemia can be seen as early as 2-3 years after the drug is given.

Mitotic inhibitors are often plant alkaloids and other compounds derived from natural products. They can stop mitosis or inhibit enzymes from making proteins needed for cell reproduction. These drugs work during the M phase of the cell cycle, but can damage cells in all phases. They are used to treat many different types of cancer including breast, lung, myelomas, lymphomas, and leukemias. These drugs are known for their potential to cause peripheral nerve damage, which can be a dose-limiting side effect. Examples of mitotic inhibitors include: the taxanes, such as paclitaxel (Taxol®) and docetaxel (Taxotere®); epothilones, which include ixabepilone (Ixempra®); the vinca alkaloids, such as vinblastine (Velban®), vincristine (Oncovin®), and vinorelbine (Navelbine®); and estramustine (Emcyt®).

Steroids are natural hormones and hormone-like drugs that are useful in treating some types of cancer (lymphoma, leukemias, and multiple myeloma), as well as other illnesses. When these drugs are used to kill cancer cells or slow their growth, they are considered chemotherapy drugs. Corticosteroids are commonly used as anti-emetics to help prevent nausea and vomiting caused by chemotherapy, too. They are also used before chemotherapy to help prevent severe allergic reactions (hypersensitivity reactions). Examples include prednisone, methylprednisolone (Solumedrol®) and dexamethasone (Decadron®).

Some chemotherapy drugs act in slightly different ways and do not fit well into any of the other categories. Examples include drugs such as L-asparaginase, which is an enzyme, and the proteosome inhibitor bortezomib (Velcade®).

Some other drugs and biological treatments are used to treat cancer, but are not usually considered "chemotherapy." While chemotherapy drugs take advantage of the fact that cancer cells divide rapidly, these other drugs target different properties that set cancer cells apart from normal cells. They often have less serious side effects than those commonly caused by chemotherapy drugs because they are targeted to work mainly on cancer cells, not normal, healthy cells. Many are used along with chemotherapy.

As researchers have come to learn more about the inner workings of cancer cells, they have begun to create new drugs that attack cancer cells more specifically than traditional chemotherapy drugs can. Most attack cells with mutant versions of certain genes, or cells that express too many copies of a particular gene. These drugs can be used as part of primary treatment or after treatment to maintain remission or decrease the chance of recurrence. Only a handful of these drugs are available at this time. Examples include imatinib (Gleevec®), gefitinib (Iressa®), erlotinib (Tarceva®), sunitinib (Sutent®) and bortezomib (Velcade®).

Differentiating agents act on the cancer cells to make them mature into normal cells. Examples include the retinoids, tretinoin (ATRA or Atralin®) and bexarotene (Targretin®), as well as arsenic trioxide (Arsenox®).

Hormone therapy includes the use of sex hormones, or hormone-like drugs, that alter the action or production of female or male hormones. They are used to slow the growth of breast, prostate, and endometrial (uterine) cancers, which normally grow in response to natural hormones in the body. These cancer treatment hormones do not work in the same ways as standard chemotherapy drugs, but rather by preventing the cancer cell from using the hormone it needs to grow, or by preventing the body from making the hormones. Examples include: the anti-estrogens—fulvestrant (Faslodex®), tamoxifen, and toremifene (Fareston®); aromatase inhibitors—anastrozole (Arimidex®), exemestane (Aromasin®), and letrozole (Femara®); progestins megestrol acetate (Megace®); estrogens; anti-androgens—bicalutamide (Casodex®), flutamide (Eulexin®), and nilutamde (Nilandron®); and LHRH agonists—leuprolide (Lupron®) and goserelin (Zoladex®).

Some drugs are given to people with cancer to stimulate their natural immune systems to more effectively recognize and attack cancer cells. These drugs offer a unique method of treatment, and are often considered to be separate from chemotherapy. Compared to other forms of cancer treatment such as surgery, radiation therapy, or chemotherapy, immunotherapy is still relatively new. There are different types of immunotherapy. Active immunotherapies stimulate the body's own immune system to fight the disease. Passive immunotherapies do not rely on the body to attack the disease; instead, they use immune system components (such as antibodies) created outside of the body. Types of immunotherapies include: monoclonal antibody therapy (passive immunotherapies)—rituximab (Rituxan®) and alemtuzumab (Campath®); non-specific immunotherapies and adjuvants (other substances or cells that boost the immune response)—BCG, interleukin-2 (IL-2), and interferon-alpha; immunomodulating drugs—thalidomide and lenalidomide (Revlimid®); cancer vaccines (active specific immunotherapies)—although several vaccines are being studied, there are no FDA-approved vaccines to treat cancer (American Cancer Society, Inc. website, 2009).

The administration of botulinum toxin directly to cancer cells is also being used to treat the growth of tumors. The anaerobic, gram positive bacterium *Clostridium botulinum* produces a potent polypeptide neurotoxin, referred to as botulinum toxin. To date seven immunologically distinct botulinum neurotoxins have been characterized: serotypes A, B, $C_1$, D, E, F, and G. Of these, botulinum toxin serotype A is recognized as one of the most lethal naturally occurring agents.

It is thought that botulinum toxins bind with high affinity to cholinergic motor neurons, are transferred into the neuron and effectuate blockade of the presynaptic release of acetylcholine. All of the botulinum toxin serotypes are purported to inhibit release of acetylcholine at the neuromuscular junction. They do so by affecting different neurosecretory proteins and/or cleaving these proteins at different sites. For example, botulinum toxin serotype A is a zinc endopeptidase which can specifically hydrolyze a peptide linkage of the intracellular, vesicle associated protein SNAP-25. Botulinum toxin serotype E also cleaves the 25 kiloDalton (kD) synaptosomal associated protein (SNAP-25), however, serotype E binds to a different amino acid sequence within SNAP-25. It is believed that differences in the site of inhibition are responsible for the relative potency and/or duration of action of the various botulinum toxin serotypes.

Currently, botulinum toxins have been used in clinical settings for the treatment of neuromuscular disorders characterized by hyperactive skeletal muscles. Botulinum toxin serotype A was approved in 1989 by the U.S. Food and Drug Administration (FDA) for the treatment of blepharospasm, strabismus, and hemifacial spasm in patients over the age of twelve. In 2000, the FDA approved commercial preparations of botulinum toxin serotype A and serotype B for the treatment of cervical dystonia, and in 2002 the FDA approved botulinum toxin serotype A for the cosmetic treatment of certain hyperkinetic (glabellar) facial wrinkles. In 2004, the FDA approved botulinum toxin for the treatment of hyperhidrosis. Non-FDA approved uses include treatment of hemifacial spasm, spasmodic torticollis, oromandibular dystonia, spasmodic dysphonia and other dystonias, tremor, myofascial pain, temporomandibular joint dysfunction, migraine, and spasticity.

Clinical effects of peripheral intramuscular botulinum toxin serotype A are usually seen within 24-48 hours of injection and sometimes within a few hours. When used to induce muscle paralysis, symptomatic relief from a single intramuscular injection of botulinum toxin serotype A can last approximately three months, however, under certain circumstances effects have been known to last for several years.

Despite the apparent difference in serotype binding, it is thought that the mechanism of botulinum activity is similar and involves at least three steps. First, the toxin binds to the presynaptic membrane of a target cell. Second, the toxin enters the plasma membrane of the effected cell wherein an endosome is formed. The toxin is then translocated through the endosomal membrane into the cytosol. Third, the botulinum toxin appears to reduce a SNAP disulfide bond resulting in disruption in zinc (Zn++) endopeptidase activity, which selectively cleaves proteins important for recognition and docking of neurotransmitter-containing vesicles with the cytoplasmic surface of the plasma membrane, and fusion of the vesicles with the plasma membrane. Botulinum toxin serotypes B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin serotype A complex can be produced by Clostridial bacterium as 900 kD, 500 kD and 300 kD forms. Botulinum toxin serotypes B and $C_1$ are apparently produced as only a 500 kD complex. Botulinum toxin serotype D is produced as both 300 kD and 500 kD complexes. Finally, botulinum toxin serotypes E and F are produced as only approximately 300 kD complexes. The complexes (e.g molecular weight greater than about 150 kD) are believed to contain a non-toxin hemagglutinin protein and a non-toxin and non-toxic nonhemagglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. By contrast, botulinum toxin serotypes $C_1$, D, and E are synthesized by nonproteolytic strains and are therefore typically unactivated when recovered from culture. Botulinum toxin serotypes B and F are produced by both proteolytic and nonproteolytic strains and therefore can be recovered in either the active or inactive form. However, even the proteolytic strains that produce, for example, botulinum toxin serotype B only cleave a portion of the toxin produced. The exact proportion of nicked to unnicked molecules depends on the length of incubation and the temperature of the culture. Therefore, a certain percentage of any preparation of, for example, the botulinum toxin serotype B toxin is likely to be inactive, possibly accounting for a lower potency of botulinum toxin serotype B as compared to botulinum toxin serotype A. The presence of inactive botulinum toxin molecules in a clinical preparation will contribute to the overall protein load of the preparation, which has been linked to increased antigenicity, without contributing to its clinical efficacy.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin serotype A can be produced from the Hall A strain of *Clostridium botulinum* with characteristics, of $3\times10^7$ U/mg, an $A_{260}/A_{278}$ of less than 0.60 and a distinct pattern of banding on gel electrophoresis. The known Shantz process can be used to obtain crystalline botulinum toxin serotype A, as set forth in Shantz, E. J., et al, Properties and use of Botulinum toxin and Other Microbial Neurotoxins in Medicine, Microbiol Rev. 56: 80-99 (1992). Generally, the botulinum toxin serotype A complex can be isolated and purified from an anaerobic fermentation by cultivating *Clostridium botulinum* serotype A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline botulinum toxin serotype A complex with a specific potency of $3\times10^7$ LD$_{50}$ U/mg or greater. This known process can also be used, upon separation out of the non-toxin proteins, to obtain pure botulinum toxins, such as for example: purified botulinum toxin serotype A with an approximately 150 kD molecular weight with a specific potency of $1$-$2\times10^8$ LD$_{50}$ U/mg or greater; purified botulinum toxin serotype B with an approximately 156 kD molecular weight with a specific potency of $1$-$2\times10^8$ LD$_5$ U/mg or greater, and; purified botulinum toxin serotype F with an approximately 155 kD molecular weight with a specific potency of $1$-$2\times10^7$ LD$_5$ U/mg or greater.

Already prepared and purified botulinum toxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

The pattern of toxin spread within a muscle has been demonstrated to be related to concentration, volume and location of injection site.

Several patents and applications relate to treating cancers with a neurotoxin and specifically a botulinum toxin. Uniformly, the methods directly deliver botulinum toxin to the cancerous cells with the goal of directly affecting the cancerous cells or their innervation. The goal has been to deliver the toxin into the cancerous cell to exert an effect, or to locally denervate a cancerous cell. By getting the toxin into a cell, botulinum toxin may inhibit the process of exocytosis from the cancer cell, which is the release of a cell's intracellular contents or vesicles into the extracellular space. These patents and applications pertain to the inhibition of exocytosis of a cancer cell and its reduced ability to divide and move. By locally denervating a cancer cell, it may become less active.

Patent application US 2005/0031648 A1, Methods for Treating Diverse Cancers, relates to the treatment of hyperplastic, precancerous or cancerous tissues with a botulinum neurotoxin by locally administering the botulinum toxin to the hyperplastic, precancerous or cancerous tissue or to the vicinity of cancerous tissue.

Patent application WO 2005/030248 relates to a method of increasing the entry of a *Clostridium botulinum* C3 exotransferase unit into cancer cells by linking the C3 to a cell-permeable fusion protein. The treatment pertains to the prevention of the cancer cell from contracting and spreading. The described compound specifically targets a cancer cell.

US 2002/0094339 A1, U.S. Pat. No. 6,565,870 B1 and U.S. Pat. No. 6,139,845 all relate to the treatment of tumors, cancers and disorders with a botulinum toxin. The toxin is injected directly into the diseased tissue to exert its effect on inhibiting exocytosis.

Citation or identification of any document in this application is not an admission that such document is available as prior art to the present invention.

SUMMARY OF THE INVENTION

The present invention provides a method of treating a cancer using a neurotoxin, preferably botulinum toxin, either alone or in combination with an anti-cancer drug or therapy. Neurotaoxin administered to the non-neoplastic tissue around a neoplasm (i.e., avoiding the neoplasm) acts to decrease the squeezing effect of contractile cells on the spread of neoplastic cells through tissue and through tubules draining the neoplasm. In certain embodiments, the methods described herein paralyze the lymphatic muscle that squeezes neoplastic cells and lymph through the circulation. In certain embodiments, the methods described herein also positively modulate the immune system to enhance cellular or humoral mechanisms against the neoplasm. Following administration of botulinum toxin around a neoplasm, regional and distant spread is reduced or eliminated.

It is an object of the invention to administered botulinum neurotoxin in such a way that a therapeutically effective amount of the botulinum neurotoxin surrounds but does not penetrate a neoplasm. It is another object of the invention to administer botulinum toxin to inhibit growth, invasion or spread of neoplasic cells. The methods described herein are easily adapted to, for example, cancer therapy at the time a cancer is initially diagnosed and could significantly improve the outcome of a patient diagnosed with cancer by reducing local, regional or distant spread of the cancerous cells. In certain embodiments, the methods described herein may be used for patients undergoing either surgery, radiation therapy, chemotherapy or other forms of treatment for the diagnosed cancer. It may also be used as a sole modality of therapy.

It is yet another object of the invention to administer botulinum neurotoxin, alone or in combination with an anti-cancer drug, topically or by injection into the non-neoplastic tissue adjacent to a neoplasm. The botulinum neurotoxin may be administered via a single injection or multiple injections. The botulinum neurotoxin may also be administered by aerosol for the treatment of, for example, lung cancer. It is understood that the neurotoxin may be applied to the non-metastatic/non-cancerous tissue around a metastasis to induce the desired effects.

It is still another embodiment of the invention that the botulinum neurotoxin, alone or in combination with an anti-cancer drug, may be injected into local, regional or distant lymphoid tissue which can be done with visual (eye or scope) or radiographic guidance such as a CAT scan or ultrasound guidance.

It is another object that the botulinum neurotoxin, alone or in combination with an anti-cancer drug, may be applied to, but not limited to the following sites: regional muscles (even at the microscopic level) area surrounding regional lymphoid tissues (if the cancer were present on a mucosal surface); the regional nodal basins; the thymus; spleen; and bone marrow or other hematopoietic sites.

It is an object of the invention that treatment with botulinum toxin, alone or in combination with an anti-cancer drug, may be applicable to other diseases characterized by a poor cellular or humoral response. In one embodiment, botulinum toxin, alone or in combination with an anti-cancer drug, may be injected locally into areas characterized by a poor cellular or humoral response, such as into the pancreas in the patient with insulin dependent diabetes, into the mucosa of the nose in a patient with fungal sinusitis, into the wart in the patient with veruca vulgaris or into a wound in the patient with a non-healing wound, or into the thymus, spleen or bone marrow in the case of a patient with immunodeficiency.

In one embodiment, the present invention provides for a method of inhibiting the growth or metastasis of a neoplasm in a patient, comprising applying to the non-neoplastic area around said neoplasm a therapeutically effective amount of botulinum neurotoxin, wherein the therapeutically effective amount of botulinum neurotoxin does not penetrate the neoplasm. In one embodiment, the neoplasm is selected from the group consisting of digestive/intestinal, nervous system, heptobiliary, genitourinary, breast, respiratory, integament, musculoskeletal, hematopoietic, sensory organ, endocrine or neoendocrine neoplasms. In another embodiment, the botulinum toxin is botulinum toxin type A. In yet another embodiment, the botulinum toxin is botulinum toxin type B.

In a further embodiment, the dose of botulinum toxin does not exceed 500 units per application. In one embodiment, the dose of botulinum toxin is between 0.01 and 100 units per application. In another embodiment, the dose of botulinum toxin is between about 1 unit to about 50 units per application, in yet another embodiment, the botulinum toxin is applied topically, by inhalation or by injection.

In one embodiment, the neurotoxin is applied by injection.

The present invention also provides a method of inhibiting the metastasis of a neoplasm in a patient which comprises comprising injecting a therapeutically effective amount of a botulinum neurotoxin into a regional or distal lymph node or nodes, regional or distal nodal tissue, thymus, spleen or bone marrow of the patient. In one embodiment, the botulinum toxin is botulinum type A neurotoxin.

The present invention further provides a method of treating a non-cancerous disease in a human characterized by reduced NK cell numbers, function or activity, comprising: a) applying to, applying to its vicinity, or applying to an area outside the vicinity of tissue affected by said disease a therapeutically effective amount of botulinum toxin; b) applying a therapeutically effective amount of said botulinum toxin to one or more lymph nodes which are proximate to said affected tissue; and c) optionally applying a therapeutically effective amount of said botulinum toxin to one or more lymph nodes which are distal to said affected tissue. In one embodiment, the neurotoxin is injected into the spleen, the thymus or both the spleen and the thymus. In one embodiment, the botulinum toxin is botulinum toxin type A. In another embodient, the botulinum toxin is botulinum toxin type B. In one embodiment of the present invention, the disease is selected from the group consisting of viral infections, viral diseases, viral-induced growths, autoimmune disease, multiple sclerosis, chronic wounds, rheumatoid arthritis, myasthenia gravis, HIV, chronic fatigue syndrome and hepatitis.

In yet other embodiments, the present invention provides a method of treating a symptom of a neoplasm in a patient, comprising applying to the non-neoplastic area around said neoplasm a therapeutically effective amount of botulinum neurotoxin, wherein the therapeutically effective amount of botulinum neurotoxin does not penetrate the neoplasm.

In one embodiment, the neurotoxin denervates muscle tissue surrounding the neoplasm and/or minimizes and/or stops lymphatic flow in the region outside of the neoplasm.

In another embodiment, the botulinum toxin weakens contraction of muscle fibers in the non-neoplastic tissue around the neoplasm.

In other embodiments, the present invention also provides a method of inhibiting the growth or metastasis of a neoplasm in a patient which comprises administering to the non-neoplastic area around said neoplasm a therapeutically effective amount botulinum neurotoxin in combination with an anti-cancer drug or anti cancer therapy, wherein the therapeutically effective amount of botulinum neurotoxin does not penetrate the neoplasm. In one embodiment, the botulinum neurotoxin is administered before the anti-cancer drug or anti-cancer therapy is administered. In another embodiment, the botulinum neurotoxin is administered together with the anti-cancer drug or anti-cancer therapy. In certain embodiments, the anti-cancer drug is selected from the group consisting of an alkylating agent, an antimetabolite, an anthracycline, mitoxantrone, topoisomerase, a mitotic inhibitor, a steroid, a differentiation agent, a hormone, or an immunotherapy agent. In another embodiment, the mitotic inhibitor is selected from the group consisting of a taxane, an epothilone, and a vinca alkaloid. In one embodiment, the taxane is paclitaxel or docetaxel. In another embodiment, the taxane is paclitaxel.

BRIEF DESCRIPTION OF THE DRAWINGS

The following detailed description, given by way of example, but not intended to limit the invention solely to the specific embodiments described, may be understood in conjunction with the accompanying drawings, in which:

FIG. 1 shows a graphic representation of mean relative tumor volumes for each measurement day discussed in Example 14.

FIG. 2 shows a model of growth of individual tumors discussed in Example 14.

DETAILED DESCRIPTION OF THE INVENTION

The present invention treats non-neoplastic (e.g., normal, non-diseased, non-cancerous) cells in order to treat a neoplasm. Treatment means to reduce, prevent or eliminate neoplastic cells or the spread of neoplastic cells or the symptoms of a neoplasm in the regional or systemic circulation. The present invention treats non-cancerous (benign), precancerous, and cancerous (malignant) conditions, as well as viral mediated growths or disorders, chronic infections and immune-mediated disorders by injecting botulinum toxin away from the site of origin of the neoplasm, condition, growth, infection or disorder. Botulinum toxin injections may reduce or eliminate the symptoms of the neoplasm, condition, growth, infection or disorder.

As used herein, the term "neoplasm" includes benign (non-cancerous), pre-cancerous, or cancerous (malignant) tumors. The phrase "neoplastic cells" includes benign (non-cancerous), pre-cancerous, or cancerous (malignant) cells originating from a neoplasm. The phrase "non-neoplastic cells" refers to normal, healthy cells not originating from a neoplasm. Non-neoplastic cells are non-pre-cancerous, non-cancerous, non-diseased cells.

"Botulinum neurotoxin" may mean a botulinum neurotoxin as either pure toxin or complex. In one embodiment, the botulinum neurotoxin may be botulinum neurotoxin serotype A, B, $C_1$, D, E, F and G. In another embodiment, the botulinum neurotoxin is serotype A or serotype B. In yet another embodiment, the botulinum neurotoxin is serotype A.

The present method relies on the well-known affinity of botulinum toxin for muscle, specifically the muscle that surrounds a neoplasm. Because of the extremely high affinity of the toxin for muscle, this method poses a significant advantage over other methods that inject botulinum toxin directly into the neoplasm in that much smaller doses of toxin may be used to elicit an effect. The smaller doses will result in fewer dose-related side effects such as the inadvertent spread of toxin through the tissues to neighboring structures, and resistance to future botulinum injections. There will be limited spread of the toxin to the neoplasm since the toxin rapidly binds to the neuromuscular junction at the injection site. In fact, previous studies have shown that botulinum neurotoxin A complex, when injected into musculature, spreads no further than about a 7-8 mm distance (Tang-Liu, et al. "Intramuscular injection of 125I-botulinum neurotoxin-complex versus 125I-botulinum-free neurotoxin: time course of tissue distribution," Toxicon 42 (2003) 461-469). Furthermore, even if the toxin were to spread to the neoplasm, it is unlikely that the small amount would be therapeutically effective, especially considering that neoplastic cells have little affinity for the toxin substrate. In certain embodiments of the invention, the doses utilized are FDA approved for use in other neuromuscular conditions that are treated with botulinum toxin.

The present invention intentionally avoids the neoplasm or its vicinity. As defined herein, the vicinity of a neoplasm refers to a distance that is typically within 7 mm from the edge or periphery of the neoplasm. Thus, if botulinum toxin is administered outside or away from the vicinity of the neoplasm, the toxin is generally administered at a distance of at least 7 mm from the neoplasm. It is known in the art that even when administered at high doses (e.g., ~70 units of botulinum neurotoxin complex), the majority of the toxin remains within about 7-8 mm of the site of injection (Tang-Liu et al.). Since the application is not by needle injection into a neoplasm, there is no risk of inadvertently seeding neoplastic cells into surrounding tissue, and there is no risk of creating a local pressure gradient that could push neoplastic cells into surrounding tissue or into penetrated blood vessels or lymphatic channels.

In one embodiment of the invention, a therapeutic amount of botulinum neurotoxin is applied to the non-neoplastic area around the neoplasm, wherein the therapeutically effective amount of botulinum neurotoxin does not penetrate the neoplasm. As used herein a "therapeutically effective amount" of botulinum toxin refers to an amount that is sufficient to reduce the spread of neoplastic cells from the neoplasm or to reduce the growth of the neoplasm.

The therapeutically effective amount of the botulinum neurotoxin administered according to a method of the disclosed invention may vary according to age, weight, height, sex, muscle mass, area of target region, number of application sites, skin thickness, responsiveness to therapy and other patient variables known to the attending physician. The amount may also depend on the solubility characteristics of the botulinum neurotoxin chosen. Methods for determining the appropriate dosage are generally determined on a case by case basis by the attending physician. Such determinations are routine to one of ordinary skill in the art (See for example, Harrison's Principles of Internal Medicine (1998), edited by Anthony Fauci et al., 14$^{th}$ edition, published by McGraw Hill).

Botulinum neurotoxins for use according to the present invention may be stored in lyophilized, vacuum dried form in containers under vacuum pressure or as stable liquids. Prior to lyophilization the botulinum toxin may be combined with pharmaceutically acceptable excipients, stabilizers and/or carriers, such as albumin. The lyophilized material may be reconstituted with saline or water to create a solution or composition containing the botulinum toxin to be administered to the patient.

Other preparations of botulinum toxin are as follows:
Type A (Dysport®): Powder for solution for injection. Uncoloured Type I glass vial containing a sterile white lyophilized powder.
Type B toxin (Myobloc®) Botulinum toxin type B (Myobloc®) is commercially available as a clear, colorless to light yellow solution of the drug in sterile water for injection. Each vial of Myobloc® injection contains 5000 units/mL of botulinum toxin type B; each mL of the injection also contains 0.5 mg of albumin human (to minimize adsorption of the toxin to the glass vial), 2.7 mg of sodium succinate, and 5.8 mg of sodium chloride. The commercially available injection of botulinum toxin type B (Myobloc®) has a pH of approximately 5.6.

Although the composition may only contain a single type of neurotoxin, such as botulinum neurotoxin serotype A, as the active ingredient to suppress neurotransmission, other therapeutic compositions may include two or more types of neurotoxins. For example, a composition administered to a patient may include botulinum neurotoxin serotype A and botulinum neurotoxin serotype B. Administering a single composition containing two different neurotoxins may permit the effective concentration of each of the neurotoxins to be lower than if a single neurotoxin is administered to the patient while still achieving the desired therapeutic effects.

Typically, about 0.1 unit to about 50 units of a botulinum neurotoxin serotype A (such as BOTOX®) may be administered per site (e.g., by injection or topical application), per patient treatment session. For a botulinum neurotoxin serotype A such as DYSPORT®, about 0.2 units to about 125 units of the botulinum neurotoxin serotype A may be administered per injection site, per patient treatment session. For a botulinum neurotoxin serotype B such as MYOBLOC®, about 10 units to about 1500 units of the botulinum neurotoxin serotype B may be administered per injection site, per patient treatment session.

In one embodiment, for BOTOX®, about 0.1 unit to about 20 units may be administered; for DYSPORT®, about 0.2 unit to about 100 units may be administered; and, for MYOBLOC®, about 40 units to about 1000 units may be administered per injection site, per treatment session.

In another embodiment, for BOTOX®, about 0.5 unit to about 15 units may be administered; for DYSPORT®, about 1 unit to about 75 units may be administered; and for MYOBLOC®, about 100 units to about 750 units may be administered per injection site, per patient treatment session.

In one embodiment, the neurotoxin may be delivered in multiple doses for each patient treatment session. In another embodiment the neurotoxin may be delivered in about 1 to about 10 doses, depending on patient variables. In yet another embodiment the total therapeutically effective dose administered (e.g., about 0.1 unit to about 50 units) is divided evenly amongst multiple injection sites.

The concentration of botulinum toxin will depend on the type of botulinum neurotoxin used and on the target location to which the toxin is applied.

In some embodiments, the present invention potentiates anti-cancer therapy. When administered in combination with an anti-cancer drug or anti-cancer therapy, botulinum neurotoxin potentiates, or increases the efficacy, of the anti-cancer drug or anti-cancer therapy. For example, in certain embodiments the anti-cancer drug or anti-cancer therapy is more effective in treating a neoplasm when botulinum toxin is first administered to the non-neoplastic tissue around the neoplasm. In one embodiment of the invention, the botulinum toxin prevents the spread of neoplastic cells from the neoplasm and prevents and/or reduces the growth of the neoplasm prior to administration of the anti-cancer drug or anti-cancer therapy.

In one embodiment of the invention, the anti-cancer drug may be, but is not limited to, an alkylating agent, an antimetabolite, an anthracycline, mitoxantrone, topoisomerase, a mitotic inhibitor, a steroid, a differentiation agent, a hormone, or an immunotherapy agent. In another embodiment the anti-cancer drug may be a mitotic inhibitor, including but not limited to the taxanes, such as paclitaxel (Taxol®) and docetaxel (Taxotere®); epothilones, which include ixabepilone (Ixempra®); the vinca alkaloids, such as vinblastine (Velban®), vincristine (Oncovin®), and vinorelbine (Navelbine); and estramustine (Emcyt®).

The present invention distantly modulates the immune system to enhance immunologic activity against cancer, metastases, precancerous conditions, viral mediated growths or disorders, chronic infections and immune-mediated disorders. A distant injection into a lymph node, regional lymphatic tissue or immunologic producing or enhancing structure (such as the spleen or thymus) may enhance lymphocytic or humoral responses against the condition.

In treating non-cancerous conditions such as viral infections, viral diseases, viral-induced growths, autoimmune diseases, multiple sclerosis, chronic wounds, chronic infections, bone infections, rheumatoid arthritis, myasthenia gravis, HIV, chronic fatigue syndrome and hepatitis the neurotoxin can be administered in the same way, and using the same dosages, as it is administered to treat neoplasms. That is, the neurotoxin can be applied to the area around the diseased or affected tissue as well as optionally to proximate and/or distal lymph nodes, the thymus, the spleen and/or the bone marrow.

There are, however, several other optional methods of applying neurotoxin to treat these non-cancerous conditions.

For example, where a specific area of diseased or affected tissue can be identified, the neurotoxin can be injected directly into the diseased or affected tissue. Thus, if a patient is suffering from type 1 diabetes, neurotoxin can be injected directly into the pancreas. For multiple sclerosis, the neurotoxin is injected intrathecally. For chronic infections, viral infections, viral diseases and viral induced growths, the neurotoxin can be directly injected into the affected tissues. For hepatitis, neurotoxin can be injected directly into the liver. For Sjogren's syndrome, the neurotoxin can be injected directly into the moisture producing glands.

For treating an autoimmune disease that affects blood vessels, the neurotoxin can be applied to the tissues surrounding the blood vessels, allowing diffusion of the neurotoxin into the blood vessels.

To treat the above conditions, the neurotoxin can also be applied to the area surrounding the affected tissue. Moreover, the neurotoxin can further be injected into the proximal lymph nodes, the distal lymph nodes, the thymus and/or the spleen.

Some conditions, such as chronic fatigue, HIV and AIDS, are systematic and do not involve a single organ system or tissue. In that event, the condition is treated by injecting the thymus, spleen or bone marrow. The lymph nodes may also be injected.

For injecting an organ or a tissue, especially one which cannot be visualized, the needle may be guided into place using conventional techniques. These techniques include, but are not limited to, palpitation, ultra sound guidance, CAT scan guidance and X-ray guidance.

Table 1 below shows several different embodiments of the present invention.

| | Type of neoplasm/cancer to be treated | | | | |
|---|---|---|---|---|---|
| | Gastrointestinal | Breast | Skin | Respiratory | Prostate |
| Location of botulinum toxin administration | mucosal submucosal muscular extraserosal | surrounding neoplasm in mammary tissue | subcutaneous intradermal subdermal deep | parenchymal | parenchymal |
| Timing of administration | at time of initial visit second visit following confirmation of cancer | same | same | same | same |
| Additional therapy | none (e.g., botulinum toxin alone) surgery chemotherapy radiation therapy ummunotherapy | same | same | same | same |
| Dose of botulinum toxin | up to 500 units administration/injection site | same | same | same | same |
| Number if injection sites | up to 10 sites | same | same | same | same |
| Method of localization | endoscopy, ultrasound guidance through endoscope, direct visualization during surgery, CT/MRI guidance | mammogram, fluoroscopy, ultrasouns or CT/MRI guidance, direct visualization during surgery | direct visualization, ultrasound guidance | CT/MRI guidance, bronoscopic, direct visualization during surgery | DT/MRI guidance, transrectal visualization, transrectal ultrasound or cytoscopic guided injection, transurethral endoscopic injection |

Botulinum Toxin

The anaerobic, gram positive bacterium *Clostridium botulinum* produces a potent polypeptide neurotoxin, botulinum toxin, which may cause a neuro-paralysis in humans. The neuro-paralysis is commonly referred to as botulism. *Clostridium botulinum* bacterium is commonly found in soil and will grow in improperly sterilized food containers. Signs and symptoms of botulism normally occur in humans within 18 to 36 hours after consuming foods containing a culture of *Clostridium botulinum*. It is thought that the botulinum toxin can pass through the lining of the gut and effect the peripheral motor neurons. The symptoms of botulinum begin with difficulty walking, swallowing, and speaking and progress to paralysis of the respiratory muscles resulting in death.

The Use of Botulinum Toxin for Cancer Therapy:
The Cholinergic Influence on Cancer:

1) Some Cancer Cells are Activated by Cholinergic Stimulation

Several forms of cancer have been demonstrated to have muscarinic cholinergic receptors that are capable of inducing mitogenesis in cells capable of undergoing cell proliferation.

Prostate: Carbachol, an acetylcholine analog, stimulates DNA synthesis in prostate cancer cells (Rayford W. et al. Muscarinic Cholinergic Receptors Promote Growth of Human Prostate Cancer Cells. The Prostate 30, 1997, abstract) and stimulation of the M3 muscarinic receptor on prostate cancer cells stimulates proliferation (Luthin G R, et al. Role of m1 receptor-G protein coupling in cell proliferation in the prostate. Life Sci 60, 1997, abstract).

Colon: M3 receptors are overexpressed in human colon cancer compared with normal colon tissue, and activation of this receptor may contribute to the malignant progression of human colon carcinoma (Yang W, et al. Cholinergic receptor up-regulates COX-2 expression and prostaglandin E2 production in colon cancer cells. Carcinogensis 21, 2000, pg. 1789). Ukegawa (Ukegawa J, et al. Growth-promoting effect of muscarinic acetylcholine receptors in colon cancer cells. J Cancer Res Clin Oncol 129, 2003, abstract) recently demonstrated that activation of the M3 muscarinic cholinergic receptor has a growth promoting effect on colon cancer cell lines.

Lung: Stimulation of the muscarinic acetylcholine receptor expressed on small cell lung carcinoma stimulates cell growth (Song P, et al. Acetylcholine is synthesized by and acts as an autocrine growth factor for small cell lung carcinoma Cancer Res 63, 2003, abstract). It has been demonstrated that small cell lung cancer cell lines synthesize and secrete acetylcholine to act as an autocrine growth factor (Song, P. et al. Acetylcholine is synthesized by and acts as an autocrine growth factor for small cell lung carcinoma. Cancer Res 63, 2003, abstract). Human mesothelioma cell growth is modulated by the cholinergic nervous system, and agonists have a proliferative effect (Trombino S, et al. Alpha-7 nicotinic acetylcholine receptors affect growth regulation of human mesothelioma cells: Role of Mitogen-activated Protein Kinase Pathway. Cancer Res 64, 2004, pg. 135). Interestingly, it has been shown that stimulation of muscarinic receptors enhanced cell-cell adhesion in small cell lung carcinoma.

Breast: Murine mammary adenocarcinoma cell lines undergo proliferation in response to carbachol that is mediated via M3 receptor activation (Espanol A, et al. Different muscarinic receptors are involved in the proliferation of murine mammary adenocarcinoma cell lines. Int J Mol Med 13, 2004, abstract).

Brain: Carbachol stimulation caused a dose and time dependent increase in proliferation of human astrocytoma cells (Guizetti M, et al. Acetylcholine as a mitogen: muscarinic receptor-mediated proliferation of rat astrocytes and human astrocytoma cells. Eur J Pharmacol 297, 1996, abstract).

Melanoma: Primary and metastatic melanoma cells reexpress muscarinic cholinergic receptors, which, when stimulated, cause cellular movements and contractions (Sailer M, et al. Induction of cellular contractions in the human melanoma cell line SK-mel 28 after muscarinic cholinergic stimulation. Anat Embryol 201:27-37, 2000). It has been hypothesized that such stimulation may be responsible for invasive growth of melanoma, and also that a cholinergic autocrine loop may be established in melanoma. In a histochemical study, muscarinic acetylcholne receptors were found to be highest in the periphery of the melanoma, at its junction with normal tissue (Lammerding-Koppel M, et al. Immunohistochemical localization of muscarinic acetylchoine receptors in primary and metastatic malignant melanomas. J Cut Pathol 25, 1997, abstract).

Lymphocytes: Human leukemic T-cells have the potential to synthesize and release acetylcholine which may play a role in regulating t-cell dependent immune responses (Fjuii T, et al. Localization and synthesis of acetylcholine in human leukemic T cell lines. J. Neurosci Rest 44, 1996, abstract).

Ovarian: In ovarian cancer, not only did a large percentage of ovarian cancers express muscarinic receptors, but such expression was associated with a reduced probability of survival (Oppitz M, et al. Muscarinic receptors in cell lines from ovarian carcinoma: negative correlation with survival of patients. Gynecol Oncol 85, 2002, abstract).

Head and Neck: Carbachol treatment of head and neck squamous cell carcinoma activates the epidermal growth factor receptor (EGFR) which plays a direct role in the regulation of the migratory behavior of head and neck cancer cells (Geschwind A, et al. Lysophosphatidic Acid-induced Squamous Cell Carcinoma Cell Proliferation and Motility Involves Epidermal Growth Factor Receptor Signal Transduction. Cancer Res 62, 2002 p. 6335). In fact, EGER activation leads to head and neck squamous cell carcinoma invasion (Geschwind A, et al. Lysophosphatidic Acid-induced Squamous Cell Carcinoma Cell Proliferation and Motility Involves Epidermal Growth Factor Receptor Signal Transduction. Cancer Res 62, 2002 p. 6335). Furthermore, the effect may be mediated by amphiregulin. In squamous cell carcinoma cells, carbachol specifically results in the release of amphiregulin (Geschwind A, et al. TACE cleavage of proamphiregulin regulates GPCR-induced Proliferation and motility of cancer cells. EMBO J. 22, 2003, abstract). Amphiregulin is known to release metalloprotease enzymes in malignant cell lines and such release may be associated with local invasiveness and metastasis (Lui, Z, et al. Regulation of matrix metalloprotease activity in malignant mesothelioma cell lines by growth factors. Thorax 58:198-203, (2003)). In non-small cell lung cancer, amphiregulin can inhibit apoptosis (Hurbin A, et al. Inhibition of apoptosis by amphiregulin via an insulin-like growth factor-1 receptor-dependent pathway in non-small cell lung cancer cell lines. Ann NY Acad Sci 1010, 2003, abstract).

2) Some Cancer Cells are Inhibited by Cholinergic Activation

It has also been demonstrated that in small cell lung carcinoma (SCLC), activation of M3 muscarinic acetylcholine receptors causes decreased cell proliferation, increased E-cadherin-mediated cell-cell adhesion, and increased Beta 1 integrin-mediated cell-substrate adhesion (Williams, muscarinic signaling in carcinoma cells, Life Sciences 72 (2003), 2173-2182). Increased cell-cell adhesion and cell-substrate adhesion would produce decreased metastases.

Cholinergic stimulation of pre-neoplastic cell line (NIH3T3) can cause both inhibitory and stimulatory growth mechanisms as well (Nicke, B. et al. Muscarinic Cholinergic Receptors activate both inhibitory and stimulatory growth mechanisms in NIH3T3 cells, J. Biol. Chem. 1999, vol. 274, no. 31, pp. 21701-21706).

3) Some Cancers are Parasympathetically Innervated

In 2001, the first report was published that demonstrated that neoplastic tissue is innervated (Seifert P, et al. Tumors may be innervated. Virchows Arch 438, 2001, abstract). In 2002, Seifert reported that papillary bladder carcinomas were parasympathetically innervated (Seifert P, et al. Nerve fibers in tumors of the human urinary bladder. Virchows Arch 440: 291-297, 2002).

4) Angiogenesis is Stimulated by Acetylcholine

Angiogenesis is comprised of sequential processes emanating from microvascular endothelial cells. The parasympathetic nervous system has been shown to positively modulate neovascularization by stimulating M3 receptors and prostaglandin E2 liberation (Heeschen C, et al. A Novel Angiogenis Pathway Mediated by Non-Neuronal Nicotinic Acetylcholine Receptors. Journal of Clin Invest 110:527-536, 2002).

5) To Block the 'Universal Docking Mechanism' in Cancer Cells

It has been theorized and demonstrated that botulinum toxin acts by inhibiting a 'universal docking mechanism' within all cells by interfering with the formation of a SNARE complex between two membranes that will fuse and undergo exocytosis. This concept has been applied to the treatment of cancer by injecting botulinum toxin directly into cancer cells. It is theorized that such an effect will help reduce a cancer cell's activity (UTS 2005/0031648 A1) or reduce actin filament association and therefore reduce a cancer cell's movement (WO 2005/030248).

There are significant practical and safety limitations to this approach. First botulinum toxin does not enter non-neuronal cells unless the cell has been permeabilized (in vitro only), a transport vehicle has been bound (in vitro only), or if a significantly higher dose of toxin has been injected. Higher does of botulinum injections may cause greater inadvertent spread with subsequent paralysis of neighboring structures, increased resistance to future injections. Other practical limitations of injecting a cancer directly with botulinum toxin include possible seeding of cancer cells to neighboring normal tissue, penetration of lymphatic vessels or blood vessels within the cancer causing a higher likelihood of spread, or producing a pressurized bolus effect on the cancer which may lead to spread.

6) Distant Injections of Botulinum Toxin Will Reduce Metastases and Provide Safer Local Therapy of Cancer To treat cancer, it is important to control not only local disease, but to control and treat distant spread called metastases. Metastases can be regional (within the neighboring lymphatic structures) or distant (far away from the primary site). Metastases generally occur by lymphatic or hematogenous spread. Spread through lymphatic channels is facilitated primarily through the contraction of skeletal or smooth muscle fibers surrounding the lymphatic network. It is well known that botulinum toxin has a strong affinity for skeletal muscle fibers and weakens or paralyzes them upon exposure. Minute amounts of toxin are needed to accomplish this and the range of doses that is needed to accomplish this is well-established for other non-cancerous conditions. Furthermore, it is well-established that the immune system is important in eliminating cancerous cells both at the primary site and within the circulation.

In certain embodiments, the methods of the present invention accomplish but are not limited to the treatment of cancer by treating cancer at the primary site by enhancing the immune response to malignant cells, preventing the spread by weakening regional contractile forces in and around lymphatic and bleed vessel structures, and treating cancerous cells within the circulation. The present invention is distinct in that the toxin is not injected directly into cancerous cells. A review of relevant anatomy follows:

1) Localization of Lymphatic Tissue

Besides blood vessels, the human body has a system of channels that collects fluid from the tissue spaces and returns it to the blood. This fluid is called lymph, and in contrast to blood, it circulates in only one direction, toward the heart.

The lymphatic capillaries originate as blind-ended, thin walled vessels. They are comprised of thin walled endothelium. These thin walled vessels ultimately converge and end up as two main trunks, the thoracic duct and the right lymphatic duct. These enter into the junction of the left internal jugular vein and the left subclavian vein, and into the confluence of the right subclavian vein and the right internal jugular vein. Interposed in the path of the lymphatic vessels are lymph nodes. The larger lymphatic vessels have a smooth muscle layer that helps propel lymph flow through the channels and unidirectional lymph flow occurs secondary to the presence of many one-way valves.

The lymphatic ducts of large size (thoracic and right lymphatic ducts) have a reinforced smooth muscle layer in the middle, in which the muscles are oriented longitudinally and circularly. They contain vasa vasorum and a rich neural network (Junqueira L, Basic Histology, 1986, Lange Medical Publications, page 269)

Lymphoid Tissue

The spleen, thymus and bone marrow are also considered lymphoid tissue. These lymphoid organs are classified as either being central or peripheral and encapsulated (e.g. spleen or lymph nodes) or unencapsulated (e.g. tonsils, peyers patches in the intestine, lymphoid nodules found throughout the mucosa of the alimentary, respiratory, urinary and reproductive tract). (Junqueira L, Basic Histology, 1986, Lange Medical Publications, page 269)

In general, lymphoid cells begin in a 'central' lymphold organ where lymphoid precursors undergo antigen-independent proliferation and acquire surface antigens that mark them as committed to either the cellular or humoral immune response. The thymus is the central organ where lymphocytes take on the capacity to participate in the cellular immune response (T cells). Cells migrate through the blood from the bone marrow to the thymus, where they proliferate, giving rise to T cells These lymphocytes are responsible for cell-mediated immune reactions. The bone marrow is where progenitor cells differentiate into humoral immune cells (B-cells) which ultimately become plasma cells and secrete immunoglobulins and provide the humoral immune response. Lymphocytes leave the central lymphoid organs and populate specific regions of "peripheral" lymphoid organs, such as lymph nodes, spleen, peyer's patchs and diffuse unencapsulated lymphoid tissue in the mucosa of the digestive, respiratory, urinary and reproductive tracts (Junqueira L, Basic Histology, 1986, Lange Medical Publications, page 269).

Spleen: The spleen is the largest lymphatic organ in the circulatory system. The spleen is a site of formation of activated lymphocytes. It serves to filter and modify the blood.

Thymus: The thymus is a central lymphoid organ located in the mediastinum. There is intense lymphocytic proliferation that occurs in the thymus during embryonic through pre-pubertal development. This is where cells proliferate that become T lymphocytes, the cells responsible for cell-mediated immunity. From the thymus, these T cells leave through blood vessels to populate the peripheral lymphoid organs, especially lymph nodes and the spleen.

Bone Marrow The bone marrow is also a central organ, but it gives rise to B cells, which ultimately differentiate into plasma cells and secrete antibodies (the humoral immune system). After differentiation, the B cells travel to lymph nodes, the spleen and especially Peyer's patches in the intestine (Junqueira, supra, page 312).

Lymph Nodes: Lymph nodes are encapsulated areas of peripheral lymphoid tissue. They are distributed throughout the body, always along the course of lymphoid vessels, which carry lymph into the thoracic and lymphatic ducts (Junqueira, supra, page 313). Lymph nodes are aggregated in particular sites such as the neck, axillae, groins and para-aortic region. The precise location of lymph nodes is well-known. See, e.g., Le, UAMS Department of Anatomy—Lymphatics Tables (Jul. 16, 2005), which is incorporated herein by reference in its entirety.

Lymph enters the lymph nodes through the afferent lymphatic channel and exits through the efferent channel. Flow is unidirectional. As lymph flows through the sinuses, 99% or more of the antigens or other debris are removed by the phagocytic activity of the macrophages within the node. Some of the material is trapped on the surface of dendritic cells, which is then exposed on the surface of the dendritic cell and recognized and acted upon by immunocompetent lymphocytes. The parenchyma of a lymph node has three general regions, the cortex, paracortex and medulla.

In the cortex, if a B cell recognizes an antigen (and sometimes with the help of T cells) the B cell may become activated and synthesize antibodies which are released into the lymph fluid then into the circulation. Activated B cells remain within the lymph node. Unstimulated B cells pass out of the lymph node and return to the general circulation.

T cells remain predominantly in the paracortex region of the lymph node. Activated T cells pass into the circulation to reach the peripheral site. Other cell types, predominantly antigen presenting cells, reside in the paracortical region of the lymph node.

The medulla is rich in plasma cells which produce further antibodies, and macrophages.

Unencapsulated tissue: Unencapsulated lymphoid tissue can be found mainly in the loose connective tissue of many organs, mainly in the lamina propria of the digestive tract, upper respiratory tract and urinary passages (Junqueira, supra, page 323). The palatine, lingual and pharyngeal tonsils are another main site of unencapsulated lymphoid tissue. This so-called mucosa-associated lymphoid tissue (MALT) includes gut-associated lymphoid tissue (GALT), bronchial/tracheal-associated lymphoid tissue (BALT), nose-associated lymphoid tissue (NALT), and vulvovaginal-associated lymphoid tissue (VALT). Additional MALT exists within the accessory organs of the digestive tract, predominantly the parotid gland.

MALT may comprise a collection of lymphoid cells or may include small solitary lymph nodes. Stimulation of B lymphocytes leads to the production of immunoglobulin A (IgA) and IgM within the peyers patches. Additionally, epithelial surfaces contain M cells which are specialized cells that absorb, transport and present antigens to subepithelial lymphoid cells, such as CD4 type 1 helper cells, antigen presenting cells and memory cells.

A more specific discussion of lymphocytes will follow below, but generally, lymphocytes contain antigen receptors that trigger differentiation. In peripheral organs, lymphocytes interact with appropriate antigens, enlarge then divide. Some become effector cells, and others become memory cells that are responsible for the secondary immune response. To generate an immune response and for effector cells to be generated, antigen must be delivered to them. This is the job of antigen presenting cells which include dendritic cells, macrophages and Langhans cells in the epidermis.

Effector cells can be activated B- or T-cells. B-cell effector cells are plasma cells that secrete immunoglobilins into the surrounding connective tissues. T-cell effector cells are of several types and include helper T cells, suppressor T cells and cytotoxic T cells. Cells attacked include tumor and viral-infected cells. T cells and macrophages secrete lymphokines that regulate the proliferation of both B and T cells.

Lymphatic Flow

The lymphatic system is found in almost all organs except the central nervous system and the bone marrow. The lymphatic circulation is aided by the action of external forces such as the contraction of surrounding skeletal muscle on their walls. (Junqueira, supra, page 269). These forces cause transportation along lymphatic channels. Contraction of smooth muscle in the walls of the larger lymphatic vessels also helps propel lymph. The transport of lymph depends on active and passive driving forces. The active driving force resulting from intrinsic pump activity in some lymph vessels plays an important role in the propulsion of lymph flow (Hosaka K, et al. Am J Physiol Heart Circ Physiol 284, 2003, abstract) There is myogenic tone in lymph channels. It has been demonstrated that the Rho kinase pathway (which is inhibited by botulinum toxin) helps regulate the lymph pump activity (Hosaka, supra). In fact, it has been demonstrated that lymph vessels are capable of regulating flow through intrinsic mechanisms (Ferguson M K, et al. Lymphology 27(2), 1994 abstract and, Muthuchamy M, et al. Molecular and Functional analyses of the contractile apparatus in lymphatic muscle. FASEB J 17, 2003, abstract). Larger lymphatic ducts contain smooth muscle and a rich neural network (Junqueira, supra, page 269).

Several factors aid the flow of lymph fluid from tissue spaces to lymph nodes and finally to the venous bloodstream: 1) "Filtration pressure" in tissue spaces, generated by filtration of fluid under pressure from the haemal capillaries; 2) Contraction of neighboring muscles compresses the lymph vessels, moving lymph in the direction determined by the arrangement of valves; 3) Pulsation of adjacent arteries; 4) Respiratory movements and the low blood pressure in the brachiocephalic vein during inspiration; 5) Smooth muscle in the walls of lymphatic trunks is most marked proximal to their valves. Pulsatile contractions in the thoracic duct are known to occur also.

2) Lymphatics. Cancer and Metastases

Cancers spread by the lymphatic and hematogenous circulations. The lymphatic and vascular systems have numerous connections, and tumor cells may pass from one system to another. During invasion, cancer cells may enter the thin walled small lymphatic vessels and be passively transported in the lymph. Tumor emboli may be trapped in the first lymph node or nodes ("regional" nodes) encountered on their route, or they may bypass regional nodes and be transported to distant nodal groups ("skip metastases"). Recent advances in mapping of the lymphatics draining cancers have allowed surgeons to identify the lymph node draining the tumor site (the "sentinel lymph node").

Each body region usually drains into a select lymph node or group of nodes, which have been detailed precisely in anatomic studies and is known in the art. See, e.g., UAMS Department of Anatomy-Lymphatic Tables, supra, previously incorporated into this application in its entirety.

Certain factors may facilitate the entry of cancer cells into the circulation and lead to metastases. Physical pressure within a cancer environment may lead to dissemination of malignant cells both locally and distantly (Targarona E M, et al. World J Surg 22, 57-58, 1998, and Lacy A M, et al. Surg Endosc 1988, 12:1040-1041). Also, a 'no-touch' technique of surgical excision has been advocated to reduce the effect of 'massaging' cancer cells into the circulation through manipulation. In this technique it is important to ligate the blood supply of the tumor before attempting mobilization of the tumor. These various clinical techniques emphasize the need to minimize the direct physical manipulation of a cancer to reduce the chance of facilitating spread.

Clinically, it has been demonstrated (Hiroto M, et al. Journal of Pancreas 6(2):143-151, 2005), that all lymphatic fluid samples squeezed from resected cancerous pancreatic tissue were positive for CEA messenger RNA, urging the need to minimize the spread of draining lymphatic fluid from a cancer.

3) Botulinum Toxin Will Weaken Lymphatic Transit

The effect of botulinum toxin on skeletal muscle is well-known. In fact, it is the basis of therapy for conditions such as strabismus, dystonias and other spastic muscle conditions. The FDA has granted approval of botulinum therapy for strabismus, blepharospasm, cervical dystonias and others. The range of doses needed to paralyze various muscles in the body is well-established.

A regional injection of botulinum toxin around a cancer will exploit the well-known binding affinity of botulinum for muscle. Skeletal muscle, smooth muscle, lymphatic muscle, blood vessel muscle and pericyte muscle may be the non-limiting target of this invention. The paralysis of surrounding skeletal or smooth muscle may limit the contractile extrinsic forces on lymphatic structures that normally facilitate flow of lymph through lymphatic channels. The intrinsic muscles within lymphatic tubules may be paralyzed or weakened by botulinum therapy. The smooth muscle wall of blood vessels may be weakened as well.

Alternative Method of Treating Cancer with Distant Botulinum Toxin Injections:

In some embodiments, a method of treating cancer with distant botulinum injections relates to the ability to modify the immune system and enhance the response to cancer using botulinum toxin therapy. The basis for this relates to the cholinergic innervation of the immune system and, therefore, also relates to the treatment of other non-cancerous conditions that exist because of a poor or weakened immune response. With respect to cancer therapy, it is again important to avoid introducing the toxin to the cancer cells since exocytosis within cancer cells is important to presenting the appropriate antigens for immune recognition and destruction by the immune system. In fact, distant injections of toxin into lymphatic organs (lymph nodes, lymph tissue) are preferred.

1) Normal Immune Response to Cancer

Antitumor immune responses can be innate (natural) or acquired (adaptive). Innate immunity is mediated by cells or soluble factors which naturally exist in tissues of body fluids and can interfere with tumor growth (Whiteside T L. J. Allergy Clin Immunol 2003; 111, S677-86). The hematopoietic cells included are macrophages, granulocytes, natural killer cells, non-MHC-restricted T cells and gamma/delta T cells. Also, natural antibodies directed at the surface components of tumor cells, complement components, C reactive protein, serum amyloid protein, mannose-binding protein are also included (Whiteside, supra). Adaptive immunity is mediated by T cells which recognize tumor-derived peptides bound to self-MHC molecules expressed on antigen presenting cells (APC). These cells include cytolytic effector cells, which are CD8+ and MHC class I restricted, but also helper CD4+T cells (Whiteside, supra).

Immune responses to malignant cells can be categorized as local/regional or systemic. Local responses include tumor infiltrating leukocytes (TIL). Systemic responses exist and are measured by the peripheral circulation delayed type hypersensitivity (DTH) in patients with cancer.

2) Immune Cells in the Tumor Microenvironment

Whiteside, supra, reviews the tumor microenvironment. TIL are frequently found in tumors. These cells may include cells mediating innate and adaptive immunity. A variety of soluble products such as cytokines and antibodies may be released in the microenvironment as well. Theoretically these products combined with direct interactions of infiltrating effector cells should result in cancer cell death, but because of the mechanisms outlined above, this often does not occur.

T cells are found in the greatest abundance of all mononuclear tumor infiltrates. It has been demonstrated that T cells in the tumor microenvironment include CD4+ (helper) and CD8+ (suppressor) cells. They have been demonstrated to be dysfunctional in cancer patients and the magnitude of their dysfunction may be related to the prognosis and survival in patients with cancer. Traditionally, the protective T cell response to tumors has been ascribed to CD8 T lymphocytes with cytotoxic activity, which are restricted by MHC Class I molecules, but recently CD4 cells have been considered to play an anti-tumor role (Gerloni M, et al. Springer Seminars in Immunopathology, Springer-Veriag 2005, 1-15). In general, both cellular and antibody-mediated responses are used for anti-tumor responses. Antibody responses are best suited for extracellular pathogens and antigens, and cell-mediated responses are best suited for intracellular pathogens and tumor cells (Gerloni, supra). Since tumor antigens are always endogenous antigens, tumors may be better suited for destruction by cell-mediated immunity. Furthermore, since tumors are MHC II negative, most efforts have focused on CD8 T lymphocytes, The role of CD4 lymphocytes has been demonstrated as well, since they help activate and expand CD8 lymphocytes as well. There are two subsets of CD4 lymphocytes, the T helper 1 (Th1) and Th2 cells. Th1 cells produce interleukin-2 (IL-2), IL-12 and interferon-gamma (INF-G) and Th2 produce IL-4 and IL-5. These cytokines affect B cells and help further influence the type of antibody response to antigen activation (Gerloni, supra. CD4 cells may help activate macrophages in draining lymph nodes or in tumor tissue.

Cell-cell cooperation may also exist among CD4 cells. Gerloni, supra, has demonstrated that a CD4 cell may activate and expand other CD4 cells as well.

The production and release to the cell membrane of cellular antigens is important tumor immunity and destruction. Both MHC class I and class II-restricted antigens are involved in the anti-tumor response. Most focus on tumor immunity has focused on the role of MHC class I restricted antigens but class II antigens are important as well. Class II antigens are tissue specific, shared among various types of tumors, true common tumor antigens and viral antigens that cause tumor transformation (such as Human Papilloma Virus or Epstein Barr Virus antigens).

Natural killer cells (NK) mediate innate immunity and are well equipped to lyse tumor cells. These cells are thought to facilitate dendritic cell/T cell interactions and drive the immune response to TAA. In general it is thought that these cells are not abundant in the tumor microenvironment but this may be because of the difficulty reliably identifying them. Also, NK cells are dependent upon Interleukin-2 (IL-2) for activation, which is generally deficient in human tumors. (Whiteside, supra. NK cells are also capable of responding to virus-infected cells. NK cells play a critical role in limiting viral infections as been provided by studies with herpes virus such as cytomegalovirus (CMV), herpes simplex virus (HSV) and Epstein-Barr virus (EBV) as well as human immunodeficiency virus (HIV) (Smyth M J, et al. Molec Immunol 42 (2005) 501-510). The effector functions of NK cells, including cytotoxicity and the capacity to produce a variety of cytokines (including INF-gamma) following activation which restricts tumor angiogenesis and stimulates adaptive immunity (Smyth, supra. Clinically, enhancement of NK cell function parallels clinical improvement in, cancer patients (Lechin F, Clin Canc Research 2004, 10:8120).

B cells are also rare in most tumors except breast cancer and melanoma. The function of B cells is differentiation into antibody-producing plasma cells. In general, antibodies to TAA are found in the circulation of patients with cancer, and they are thought to be made from and secreted from tumor-draining lymph nodes, spleen or other lymphoid tissues. From there, IgG molecules are transported by plasma or lymph to tissue sites.

Dendritic cells (DC) are common in human cancers. These cells process and present TAA to naive or memory T cells, thus playing an important role in the generation of tumor-specific effector T cells. In patients with cancer, DC are sometimes dysfunctional. However, DC infiltrations into tumors have been associated with significantly prolonged patient survival and reduced incidence of recurrent or metastatic disease. Conversely, patients with lesions scarcely infiltrated with DC have a relatively poor prognosis.

Macrophages are also found in the tumors microenvironment and are called tumor associated macrophages (TAM). In tumors, TAM actually inhibit lymphocyte function including T cell proliferation and NK-mediated antitumor cytotoxicity.

3) Immune Suppression in the Tumor Microenvironment

As mentioned above, cancers can evade the immune system and thereby escape recognition. These include expression by tumors of poorly immunogenic antigens, defects in antigen processing, inadequate costimulatory interactions, production of immunosuppressive factors, or through the fact that immune cells are compromised in number and/or function (Hoffman T K, et al. Cancer Immunol Immunother (2004) 53:1055-1067).

4) Immune Effector Cells in the Circulation of Cancer Patients

Just as the local microenvironment contains dysfunctional immunocytes, the peripheral blood lymphocytes contain function irregularities as well. Signaling abnormalities, functional impairments and apoptosis are seen in T cells, NK cells, macrophages and B cells in the peripheral circulation.

5) Local Immunotherapy and Cancer Response

The ability to modulate the local immune environment is important for cancer therapy. When low doses of natural IL-2 were injected around tumor-draining lymph nodes, 65% of patients had a complete, partial or minimal response (Feinmesser M et al. Eur Arch Otorhinolaryngol (2004) 261:359-368). Unfortunately, the effect was short-lived and multiple daily or weekly injection are important (Shibuya T Y, et al. Clin Canc Research 2004, 10:7088-7099). In other studies using peritumoral infiltration of lymphokine with or without regional infiltration into the lymph nodes, similar regression was noted (Feinmesser, supra).

The administration of bioactive suture, coated with INF-gamma, IL-2, have been shown to generate a prolonged Th1 response and stimulate the secretion of IL-12 and prolong the immune response (Shibuya T Y, et al. Clin Canc Research 2004, 10: 7088-7099). In this therapy the suture is considered a carrier for the bioactive products, and is placed using a 'Seldinger technique' whereby a needle with a trochar is introduced into the desired location and the suture is subsequently passed. Placement of the suture is invasive and the suture be kept long and attached to the skin surface, 'similar to a surgical drain' which may potentially lead to infection.

In effort to enhance local immune function, cytokine genes have been transduced into the patient's tumor cells. Again the underlying concept is to stimulate a vigorous immune response by enhancing local cytokine production. Pitfalls of this technique include the reliance on tumor cells to produce an effect, and the lack of adequate quantity and quality of patient tumor cells and the heterogeneous expression of the cytokine genes. Also the tumor cells must be irradiated prior to reintroduction into the patient (Steele T A, et al. PSEBM 2000, 23:118-127).

6) Immunotherapy Strategies

In general terms, there are two forms of immunotherapy, active and passive. Active immunotherapy refers to the induction of immune responses through application of immunogenic tumor antigens (such as peptides, proteins, tumor cells or tumor lysates), whereas passive immunization relies on the transfer of immune effector molecules or immune cells (Hoffman T K, et al. Cancer Immunol Immunother (2004) 53:1055-1067).

Active immunomodulators can be nonspecific or specific. An active, nonspecific immunomodulator may include local therapy with BCG, thymic extracts or OK-432 which attempt to induce an antitumor response. Such therapy however, has not demonstrated consistent survival benefits to cancer patient. Active, specific immunomodulation may include the administration dendritic cell-based vaccines or DNA-based vaccines. Such therapy is in its infancy and is usually reserved for recurrent, end stage disease of aggressive cancers.

Passive immunomodulation is also divided into nonspecific and specific therapies. Passive, nonspecific therapy includes the administration of cytokines such as systemic interferon or interleukin or cellular adoptive transfer mechanisms such as lymphocyte activated killer cells and interleukin-2 administered locally. Results of such therapy were inconsistent and yielded high clinical toxicities. When IL-2 is administered systemically, an unacceptable rate of systemic toxicity was observed including fever, malaise, hypotension, pulmonary edema and shock. Passive specific immunomodulation includes the administration of antibodies targeted to epidermal growth factor receptor, or through cellular adoptive transfer through T cells specific for the tumor.

7) Importance of Maintaining Exocytosis for Immune Recognition

As indicated above, in order to effectively kill cancer cells, it is important that cancer cells maintain their ability to undergo exocytosis. Exocytosis is the specific process by which a cellular vesicle fuses with the plasma membrane of the cell. It is the process by which proteins and lipids that are created inside a cell are transported to the cell's exterior. (Alberts B, et al. Molecular Biology of the Cell, Third Edition 1994, Garland Publishing pg. 626).

Proteins can be secreted from cells by exocytosis in either a constitutive or a regulated manner (Alberts, supra, page 633). In the regulated pathway, molecules are stored in secretory vesicles which do not fuse with the plasma membrane to release their contents until an extracellular signal is received. Whereas this pathway only operates in specialized selected cells, a constitutive secretory pathway operates in all cells, mediated by continual vesicular transport from the trans Golgi network to the plasma membrane. (Alberts, supra, pg 633). This method allows various membrane proteins, secreted proteins and lipids to be delivered to the appropriate plasma membrane domains (Alberts, supra, p 633).

An antigen is a macromolecule that includes virtually all proteins and many polysaccharides (Alberts, supra, p 1201). These so called antigenic determinants stimulate the production of antibodies or T cell responses (Alberts, supra, p. 1201). Because the immune system works by clonal expansion, even a single antigenic determinant will activate many clones. Conversely, the alteration or down regulation of antigenic determinants may predictably significantly alter the host's immune response to a tumor antigen.

Most TAA are self-antigens that are overexpressed or altered post-transcriptionally. In order to mount an adequate response, TAA-specific T cells and innate immunity mediated by non-specific activated T cells, activated NK cells and activated macrophages are necessary. With this in mind, there are two major reasons why tumors do not induce a vigorous immune response. First, the tumor can fail to provide a proper antigen for the immune response to detect and to which the immune system can react. Second the tumor can prevent an immune response by failing to provide accessory molecules important for developing an immune response (Steele, supra).

Lack of appropriate antigen presentation can include expressing a mutant tumor protein that is not immunogenic, having a defective antigen processing pathway so that the antigen cannot be shuttled to the cell surface or by masking the tumor antigen so it cannot be seen by immune cells (Steele, supra). Without the tumor expression of important surface molecules, no antitumor response can be generated (Steele, supra. These findings emphasize the need to have an intact method of exocytosis within cancer cells to allow TAAs to be expressed on cancer cells and to elicit an immune response.

It has been demonstrated that when cancers have a higher expression of Beta-2 macroglobulin, a component of the MHC-1, the clinical outcome improves (Feinmesser M et al. Eur Arch Otorhinolaryngol (2004) 261:359-368). It is suggested that the increased antigen expression facilitates tumor-antigen presentation to CD8 lymphocytes.

In addition to the expression of TAA, exocytosis is important in metastases. Cancer metastases is a process involving a coordinated program of events that includes changes in cell adhesion, polarized proteolysis and migration, intravasation into the circulation, subsequent adhesion to endothelial cells followed by extravasation, invasion and induction of angiogenesis. Cell surface proteins and receptors are intimately involved in these processes. For example, loss of E-cadherin can reduce cell-cell adhesion and allow cancer cells to more readily escape tumors. Integrins regulate cell adhesion, motility, invasion, and angiogenesis, and metalloproteases on tumor cells can degrade the extracellular matrix. In other words, the process of exocytosis, which on one hand may release metalloprotease and contribute to primary invasion of the primary site, is integrally important in the production of adhesion molecules which help prevent metastases and the expression of antigens that may facilitate recognition and destruction by the immune system. Any attempt to globally shut down the process of exocytosis may therefore have significant drawbacks in the therapy of cancer medicine.

In fact, the treatment of cancer includes attempts to enhance the immunogenicity of tumor cells. For example, it is important for T cells to attack cancer cells is to bind to a specific peptide fragment that is presented on a cancer cell surface. It is known that tumor cells rarely express this antigen and efforts have been made to transduce costimuatory molecules in tumors to promote a vigorous antitumor immune response (Steele, supra)

8) Cholinergic Modulation of Immune Function

Cells that are normally immunoprotective from cancer include but are not limited to natural killer (NK) cells, activated macrophages, and T cells (including Tumor infiltrating lymphocytes and Natural killer T Cells) Acetylcholine inhibits natural killer cell function, which was blocked by atropine (Qiu Y H, Peng Y P, et al. Effect of acetylcholine on in vitro IL-2 production and NK cell cytotoxicity of rats. Lymphology 37(1):31-8, 2004)), suggesting that botulinum may inhibit suppression of NK cell activity. NK cells are known to induce apoptosis of malignant cells (Smyth M J, et al. Activation of NK Cell Cytotocicity. Molec Immunol 42:501-510, 2005) and inhibit metastases (Kim, S, et al. In vivo natural killer cell activities revealed by natural killer cell-deficient mice. Proc Natl Acad Sci 97, 2000, abstract), hence botulinum may enhance this activity. Pilocarpine, an acetylcholine analog, increases the CD8/CD4 ratio which was also blocked by atropine, suggesting that T cell suppressor activity is positively influenced by acetylcholine (Prync A E, Arzt E, et al. The inhibitory effect of the muscarinic agonist pilocarpine on lymphocyte activation involves the IL-2 pathway and the increase in suppressor cell function. Int J. Neurosci 62, 1992, abstract). This would suggest that a reversal of the CD8/CD4 ratio or an increase in T helper activity would positively influence cancer cytotoxicity (Gerloni M, et al. Springer Seminars in Immunopathology, Springer-Verlag 2005, 1-15) as well. Acetylcholine also reduces tumor necrosis factor production (Steinman L. Elaborate interactions between the immune and nervous systems. Nature Immunology 5, 2004, abstract). Finally, when human salivary glands were injected with botulinum toxin, it was observed that the quantitative amount of immunoglobulin (specifically IgA) secreted into the saliva increased. The above findings support the use of botulinum to locally enhance immune cytotoxicity and humoral immunity.

9) Botulinum Toxin can Modulate the Immune System

The eventual alteration of immune function that is caused by cholinergic inhibition includes enhanced cellular and humoral immunity. Enhanced NK cell function directly enhances killing of cancer cells. Enhanced NK cell activity causes secondary enhancement of cellular and humoral immunity by release of cytokines and interferon gamma. This results in increased T cell and NKT cell function, which further enhances cellular destruction of cancer.

Enhanced NK cell function has also been demonstrated to reduce metastases (Kim, supra).

Enhanced NK cell function also enhances the outcome of patients with viral infections, viral diseases, viral-induced growths, autoimmune disease (such as sjogren's disease, insulin dependent diabetes), multiple sclerosis, chronic wounds, chronic infections such as tonsillitis (Ferlazzo G, et al. Journal Immunol 2004, 172:1455-1462) or bone infections (Miyasaki K, Periodontal Immunology, Homepage, www.dent.ucla.edu), rheumatoid arthritis, myasthenia gravis and human immunodeficiency virus (HIV), all of which are conditions characterized by reduced NK cell numbers, function or activity (Baxter, A G, et al. Autoimmunity 2002, 35:1-14, and Lee P T, et al., J. Clin Invest 2002, 110:793-800). Low NK cell activity is also found in Chronic fatigue syndrome (Whiteside T L, et al., AM J Med 105, 1998, abstract), and hepatitis (Chen Y, et al., J Viral Hepatitis 12, 2005, abstract), both of which are amenable to botulinum therapy.

Injecting botulinum toxin around and outside the vicinity of cancerous cells may improve local control of cancer at the primary site, prevent the distant spread of cancer cells into the circulation and may treat cancer cells in the local environment and distant circulations. The risks (as described above) of injecting the toxin into or into the vicinity of a cancer will be avoided. Likewise, injecting botulinum toxin in this manner may enhance the outcome of patients suffering from viral infections, viral diseases, viral-induced growths, autoimmune diseases, multiple sclerosis, chronic wounds, chronic infections, rheumatoid arthritis, myasthenia gravis and HIV, etc., as described above.

Classification of Cancers Amenable to Treatment:

TABLE 1

Classification of Cancers Amenable to Treatment

| Cancer Type | Specific Examples |
|---|---|
| Digestive/Intestinal cancers | Salivary gland, lips, oral cavity, oropharyngeal, hypopharyngeal, nasopharyngeal, esophageal, stomach, small intestine, large intestine, anal |
| Nervous system cancers | Brain, nerve |
| Hepatobiliary cancers | Liver, gall bladder, pancreas, biliary tract |
| Genitourinary cancers | Kidney, ureter, bladder, urethera, prostate, penile, vaginal, vulvar, uterine, endometrial, ovarian, cervical, testicular |
| Breast cancer | |
| Respiratory cancers | nose, sinus, nasopharyngeal, laryngeal, tracheal, bronchial, lung, pleura (mesothelioma) |
| Integument cancers | melanoma squamous cell carcinoma, basal cell carcinoma, merkel cell |
| Musculoskeletal cancers | rhabdomyosarcoma, sarcomas |
| Hematopoietic cancers | lymphoma, leukemia, myelodysplasia |
| Sensory organ cancers | eye, ear |
| Endocrine cancers | thyroid, parathyroid |
| Neuroendocrine cancers | neuroendocrine cancers except for those of the adrenal medulla or glomus tumors |

The Control of Metastases is Important for the Treatment of Cancer

Inhibition of spread: Physically manipulating or squeezing a cancer at the gross or microscopic level through contractile cells may produce a physical pressure for the cancer cells to spread, or it may allow cancer cells that have already entered into an efferent channel to be squeezed into the broader circulation. For example, a well-known premise in oncologic surgery is to minimize manipulation of the cancer during resection to minimize the physical forces that may lead to entrance and spread of cancer cells into tubules such as lymphatics or blood vessels. In fact, when surgically feasible, it is desirable to initially ligate the vessels of a cancer to the cancer and minimize spread.

Botulinum Toxin Will Locally Denervate Muscular Tissue

Botulinum toxin will inhibit contraction of gross or microscopic muscular fibers around a cancer thereby inhibiting the chance of squeezing the cancer cells into the local environment or into efferent tubules that carry cancer distantly. Botulinum toxin will paralyze the lymphatic muscle that contracts to squeeze lymph and possibly cancer cells into the distant circulation.

The Ability to Positively Immunomodulate is Important for the Treatment of Cancer Botulinum may enhance local immunoglobulin production when applied to a mucosal surface. This may enhance 'tumor-killing' cells or properties of the local tissue and enhance the anti-cancer effect.

Botulinum has been shown to enhance and/or cause proliferation of a 'myoepithelial cell' which is a very specific cell type. The myoepithelial cell is considered an important defensive cell in breast cancer for unknown mechanisms. By enhancing proliferation of these myoepithelial cells, botulinum may enhance the host defense mechanism in tumors that have myoepithelial cells (breast, prostate, lung, airway, etc.).

Other unknown mechanisms may also be at play. For example, cell-cell signaling and subsequent growth/metastasis is a feature of cancer cells. It has been suggested that by altering these signals, one may alter the growth of cancer. Regarding botulinum, the signals can be chemical (e.g., substances released by exocytosis and blocked by botulinum) or physical (e.g., physical signals to surrounding cells) but either can be blocked by botulinum.

Techniques that target multiple sequences of events in cancer progression are more likely to benefit than a technique that targets only one sequence.

The invention will now be further described by way of the following non-limiting examples.

EXAMPLES

The following non-limiting example demonstrates the ability of botulinum toxin to enhance a cellular immune response:

Example #1

A patient with verruca vulgaris (common wart) is injected at the base of the wart and its periphery with a total of 25 units of botulinum toxin type A. Over 3-5 weeks, it is noticed that the size of the lesion is significantly reduced in all dimensions (by nearly 90%), is soft and is barely perceptible. After 3 months, the size of the lesion returns to its original size.

The following are non-limiting, prophetic examples of the present invention.

Example #2

A 50 year old diagnosed with invasive lung cancer undergoes local administration of 30 units of botulinum toxin type A around the cancer by bronchoscopic injection, aerosolization or transthoracic injection. The cancer is visualized either clinically or radiographically and the area around the cancer is directly injected, and the patient undergoes radiation, chemotherapy or surgery as initially planned. The local application of botulinum also enhances the patient's local immunity which serves to minimize infection during therapy, leading to fewer episodes of pneumonia and fewer interruptions in treatment because of infection. After 2 months of standard cancer therapy, it is noted that the local invasion and regional and distant spread is reduced. The patient experiences an improved clinical outcome.

In the above example, the patient's regional or distant lymph node or nodes, thymus, spleen or bone marrow can each also be injected with 1-100 units of botulinum toxin type A. The tissues are injected by radiographic guidance or direct visualization during mediastinoscopy or surgery. Following injection, it is noticed that there is an improved immunologic response to the cancer. Local control and local, regional and distant metastases are reduced. The injection may be repeated in 3-6 month intervals.

Example #3

A 50 year old man with invasive prostate cancer is injected with 40 units of botulinum toxin type A around the cancer which results in fewer regional or distant metastases. The injection is guided to the region around the cancer by radiographic guidance (CAT scan, ultrasound, MRI guidance or others). The effect of botulinum is also on local myoepithelium and the incidence of in-transit, regional and distant metastasis is reduced. The patient continues to undergo standard therapy for the prostate cancer. During the course of treatment there is less invasion of surrounding tissue and less spread of cancer cells into the regional or systemic circulation. The patient is reevaluated periodically and it is noted that the cancer and cancer-region should be reinjection in 3 months, as the patient has persistent disease that did not respond to standard therapy. 40 more units are injected and the patient continues with planned therapy. Three months later the tumor is eliminated and further injections are not required. The patient experiences an improved cure and survival.

The patient's regional or distant lymph nodes, thymus, spleen or bone marrow can each also be injected with 1-100 units of botulinum toxin type A. These tissues are injected by radiographic guidance, direct palpation or during surgery. Local control and local, regional and distant metastases are reduced. The injection may be repeated in 3-6 month intervals.

Example #4

A 60 year old female diagnosed with breast cancer is treated with 30 units of botulinum toxin type A injected around the cancer before any therapy begins. Local contraction of breast tissue is reduced and the patient experiences a reduced incidence of local, regional and distant spread. Clinical outcome is improved.

The patient's regional or distant lymph nodes, thymus, spleen or bone marrow can each also be injected with 1-100 units of botulinum toxin type A. The lymph nodes are injected by palpation, radiographic guidance or direct visualization during surgery. Following injection, it is noticed that there is an improved immunologic response to the cancer. Local control and local, regional and distant metastases are reduced. The injection may be repeated in 3-6 month intervals.

Alternatively, the patients sentinel lymph node can be identified using lymphoscintigraphy. Since these nodes are highly likely to contain metastatic cancer, they are avoided during radiographic injections, and only the surrounding nodal basin is injected.

Example #5

A 45 year old male is diagnosed with locally invasive colon cancer. At the time of diagnosis, 50 units of botulinum toxin type A are injected into and/or around the cancer to weaken the contractile effects of the gross and microscopic colonic musculature. The cancer is 'frozen' and there is less invasion of cancer cells into the surrounding tissue or lymphatic or blood vessels. The patient can undergo additional therapy (chemotherapy, radiation therapy and/or surgery) and local, regional and distal spread is reduced or eliminated.

The patient's regional or distant lymph nodes, thymus, spleen or bone marrow can each also be injected with 1-100 units of botulinum toxin type A. These tissues are injected by radiographic guidance, endoscopic injection, direct palpation or during surgery. Local control and local, regional and distant metastases are reduced. The injection may be repeated in 3-6 month intervals.

Example #6

A patient with metastatic tongue cancer is noted to have symptoms of compression and bleeding referable to local invasion of a regional metastasis. The metastasis is deemed nonoperable and he cannot receive any further radiotherapy. Alternatively, he may be treated with surgery, radiotherapy or chemotherapy. The area around the metastatic lesion is injected with 30 units of botulinum toxin type A. There is less local invasion and metastases from the lesion. The metastasis undergoes regression and compressive symptoms are reduced.

The patient's regional or distant lymph nodes, thymus, spleen or bone marrow can each also be injected with 1-100 units of botulinum toxin type A. These tissues are injected by radiographic guidance, direct palpation or during surgery. Local control and local, regional and distant metastases are reduced. The injection may be repeated in 3-6 month intervals.

Example # 7

A 35 year old male has locally invasive pharyngeal cancer. Thirty five units of botulinum toxin Type A is injected around the lesion. It is noticed that the cancer undergoes regression and is eliminated with local injections of botulinum without further therapy.

The patient's regional or distant lymph nodes, thymus, spleen or bone marrow can each also be injected with 1-100 units of botulinum toxin type A. These tissues are injected by radiographic guidance, direct palpation or during surgery. Local control and local, regional and distant metastases are reduced. The injection may be repeated in 3-6 month intervals.

Alternatively, the patient's sentinel lymph node can be identified using lymphoscintigraphy. Since these nodes are highly likely to contain metastatic cancer, they are avoided during radiographic injections, and only the surrounding nodal basin is injected.

Example #8

A patient with cancer has invasive fungal sinusitis. His white blood count is less than 1,000 and there is a poor immunologic response in the sinus cavity. He is taken to surgery for remove of the tissue invaded by the fungus. Before surgery or preferably, after removal of the tissue and during surgery, 10 units of botulinum toxin type A are injected in multiple sites into the surrounding nasal cavity. It is noted that the local immunologic and systemic immunologic responses are improved and the patient experiences a cure from the disease.

The patient's regional or distant lymph nodes, thymus, spleen or bone marrow are each injected with 1-100 units of botulinum toxin type A. These tissues are injected by radiographic guidance, direct palpation or during surgery. Local control and distant spread of the fungus are reduced. The injection may be repeated in 3-6 month intervals.

Example #9

A patient with cancer, autoimmune disease, diabetes, HIV or AIDS or lupus has toenail fungus (onychomycosis). The affected nail is injected with 5 units of botulinum toxin type A in multiple spots and there is regression of the symptoms of onychomycosis. Alternatively, the surrounding normal tissues or regional lymph nodes can be injected.

Example #10

A 10 year old patient with insulin dependent diabetes mellitus (IDDM) is dependent upon insulin injections. Botulinum toxin type A (50 units) is injected using radiographic guidance into her pancreas. It is noticed that her natural insulin levels rise and she has fewer symptoms of diabetes.

Example #11

A 40 year old woman with autoimmune disease is injected with type A botulinum toxin. 100 units of the toxin are injected into her spleen, bone marrow or regional nodal basin where the symptoms are located. Following injection, her symptoms are improved.

Example #12

A 35 year old male with AIDS has a suppressed T helper population and is susceptible to infections. 50 units of botulinum toxin type A is injected into his thymus and spleen. Alternatively, his bone marrow can be injected. The patient's T cell population increases and his condition is significantly improved.

Example #13

Clinical Trial Results

In order to histologically determine whether botulinum toxin type A can denervate muscle tissue surrounding cancer, a human clinical trial was carried out after obtaining Institutional Review Board approval. In the study, patients diagnosed with early squamous cell carcinoma of the oral cavity that were scheduled to undergo surgical excision were offered participation in the study. Ten (10) units of botulinum toxin type A (BOTOX®, Allergan) were injected preoperatively around one side of the cancer, and saline control was injected on the contralateral side. A total of 10 (ten) units of botulinum toxin were injected in two separate sites on the same side of the cancer. Each of the two injections contained 5 units of Type A botulinum toxin and each was given one centimeter away from the edge of the cancer. The two injections were also placed one centimeter apart. The injections were given 10 to 19 days preoperatively, and were given as soon as possible after making the diagnosis of cancer (1 to 4 days). Patients were taken to surgery as part of their regularly scheduled treatment plan, and the surgical specimen was additionally examined for evidence of denervation atrophy on the side of the specimen injected with botulinum toxin.

Five patients were initially enrolled in the study, although one was later excluded due to receiving non-surgical therapy. Of the remaining four patients, three had squamous cell carcinoma of the mobile tongue, and one had squamous carcinoma of the palate. Patients ranged between 36-83 years of age, and all were male. After obtaining informed consent, injections were given as soon as possible after their diagnosis of carcinoma was made, in order to maximize the duration of botulinum toxin effect before surgery. Patients were injected 10 to 19 days prior to surgery. There were no complications of injection and injections were well tolerated. It was theorized that weakening the surrounding skeletal and smooth muscle in the region around the cancer would minimize lymphatic flow and lessen the chance of metastases, thereby 'freezing' the cancer in place as soon as a diagnosis of cancer was made.

Following surgical excision of the specimens, histologic analysis revealed denervation effect in the surrounding muscle in one of the four patients. There was a partial effect noted in another patient, and no appreciable difference noted in two of the four patients. Pathologic analysis of the botulinum toxin injected muscle in patients #1 and #3 revealed no structural differences when compared to the saline-injected control side. In patient #2, there was evidence of focal myofiber atrophy with focal chronic inflammation. In patient #4, there was evidence of clusters of atrophic fibers with suggestive group atrophy. It is believed that the low dose of botulinum toxin (10 units) was responsible for the partial effect. For reference, it would not be unusual to inject 200 units of botulinum toxin into a patient with excessive underarm sweating. Since this study was the first to inject humans with cancer with botulinum toxin, the parameters of injection had never been defined, and a conservative dose was therefore used in order to minimize the chance of complications. It is possible that 10 units of type A botulinum toxin was insufficient to induce denervation of the large muscles of the tongue.

In addition, it became clear that accurately assessing for denervation atrophy from botulinum toxin is exceptionally difficult in the acute phase, known as acute denervation atrophy. Accurately assessing for botulinum toxin effect in the acute phase using static histologic techniques is difficult because the muscle fibers have not had a chance to demonstrate the ultimate effect of denervation. However, it is routine to examine a specimen for denervation atrophy after several weeks when the muscle fibers have undergone atrophy, which can be readily assessed visually and histologically.

Further, based on the present study, and further routine dosage evaluations, one of skill in the art will be able to determine appropriate dosages of botulinum toxin based on the toxin type, the location of the cancer and the size of the region surrounding the cancer to be treated.

The study demonstrated that local muscle paralysis around cancer could safely be performed in humans. Two of the four patients demonstrated focal muscle atrophy, which are findings that can be induced by botulinum toxin. These findings are consistent with the concept that focal, selective muscle weakening around a cancer can be induced by a botulinum toxin injection. The implications of this finding are far reaching and novel in cancer care. First, this technique will allow cancer care to be initiated at the immediate onset of diagnosis of cancer. Unfortunately, there is often a prolonged delay between diagnosis and treatment of cancer in most situations, because of the need for obtaining diagnostic studies, medical clearance and scheduling of the actual treatment of cancer whether it is surgery, chemotherapy, radiation or other form of therapy. Even a few short weeks may be enough window for cancer to spread from the primary site. With botulinum toxin therapy, muscle fibers are paralyzed within 24 to 48 hours of the diagnosis of cancer, thereby freezing the cancer in place.

Also, there is currently no method of providing prolonged paralysis of the conduits (lymphatics) that direct spread of cancer to distant sites. This barrier would be overcome with botulinum therapy and would be particularly helpful in patients undergoing chemotherapy, radiation therapy or other forms of gradual therapy where the cancer is not immediately removed. The effect of a single botulinum injection lasts from 2-6 months.

Example #14

In Vivo Evaluation of the Ability of Botulinum Toxin a (BTX) to Potentiate the Efficacy of the Anti-Cancer Drug Paclitaxel (Taxol®) Against the Human Colorectal Cancer Xenograft HCT-116 in Nude Mice Test substance: Botulinum Toxin A (BTX); 0.45 units/mouse; subcutaneous (4×10 µL peri-tumoral injections).
Vehicle for test substance: Sterile saline (0.9% w/v); subcutaneous (4×10 µL peri-tumoral injections).
Reference substance: Paclitaxel; 5 mg/kg; intravenous by tail vein injection.
Vehicle for reference substance: 50 µL of dimethyl sulphoxide (DMSO) followed by dilution in 5% ethanol, 10% cremaphor, 85% sterile saline (0.9% w/v)
Test system: Nude (nu/nu) athymic CD-1 mice; female; age range 6 to 8 weeks; weight range 22 to 24 g on delivery.
Number per group: 6 treatment groups; 10 mice per group.
Results: Over the 42 day measurement period, the estimated doubling time of the vehicle groups was 9.7 days, for the BTX group the estimated doubling time was 12.5 days, for Paclitaxel group the estimated doubling time was 10.5 days and for the BTX+Paclitaxel combination treatment group the estimated doubling time was 16.3 days. The reduction of tumor growth rate compared to vehicle in the BTX+Paclitaxel combination treatment group was statistically significant ($p<0.05$, analysis of covariance). The differences in growth rate between vehicle and the groups receiving Paclitaxel or BTX as single agents was not statistically significant. Administration of Paclitaxel+BTX as a combination treatment, caused an estimated doubling time delay of 6.6 days. Administration of Paclitaxel as a single agent caused an estimated doubling time delay of 0.8 days. Administration of BTX as a single agent, caused an estimated doubling time delay of 2.8 days.

The mean relative tumor volumes of mice receiving all treatments were lower than vehicle treated mice throughout the majority of the 42 day study.

From histological analysis BTX induced an increased inflammatory response in the tissue surrounding the tumors.

In nude athymic mice bearing subcutaneous human colorectal tumor HCT116 xenografts, treatment with reference substance, Paclitaxel, at 5 mg/kg i.v. in combination with test substance BTX, 0.45 units/mouse, subcutaneous (peri-tumoral) resulted in a statistically significant reduction in tumor growth rate.

Treatment with either test or reference substance as single agents did not result in a statistically significant reduction in tumor growth.

From these data it can be seen that Botulinum Toxin A (BTX) may potentiate the efficacy of a sub-maximal dose level of the anti-cancer drug Paclitaxel against the human colorectal cancer xenograft HCT-116 in nude mice.

Histological examination of tumors and surrounding tissue suggested that peri-tumoral subcutaneous administration of BTX causes an increase in tissue inflammation.

Regulatory Compliance

BTX was administered as per protocol to Groups 2 and 6 on Day 0. On Days 3 and 4 clinical signs were observed (hunched posture, prominent spines and rib cages, unsteadiness and weight loss of up to 18.6% of starting weight). Six mice in Group 2 and 5 in Group 6 were terminated as a result. These tumors were not removed and so did not form part of the histological analysis. As a result, for the remainder of the study, Groups 2 and 6 contained 4 and 5 mice, respectively.

Paclitaxel dosing should have proceeded on Day 3 but this was delayed until Day 5 to ensure that the condition of the remaining mice did not worsen. Paclitaxel dosing days therefore changed from Days 3, 7, 11, 15, 19 and 23 to Days 5, 9, 13, 17, 21 and 25.

On Day 5 two animals in Group 4 (Paclitaxel) received approximately half of the full dose volume due to difficulty injecting into the tail vein.

On Day 20, one animal was removed from Group 1 (BTX vehicle) due to tumor condition and the tumor tissue was not removed. As a result histological analysis was performed on only 9 tumors for this group.

Test Substance and Materials
Test Substance, Reference Substance and Vehicle
Test substance: Botulinum Toxin A (BTX) (batch number C2297 C2; expiry date 30 Apr. 10; solid; Allergan)
Reference substance: Paclitaxel (batch number 039K1515; expiry date 1 Sep. 11; white powder; Sigma)
Vehicle for test substance: Sterile saline (0.9% w/v) (batch number 09C24G50; expiry date 28 Feb. 2011; clear liquid; Baxter supplied by TPS Medical)
Vehicle for reference substance: 50 µL of dimethyl sulphoxide (DMSO) (batch number 1420182; expiry date 31 Dec. 10; clear liquid; Sigma) followed by dilution in 5% ethanol (batch number L687104; expiry date 30 Nov. 11; liquid; VWR), 10% cremaphor EL (batch number 1369469; expiry date 31 Dec. 09; liquid; Sigma), 85% Sterile saline (0.9% w/v) (batch number 09C24G50; expiry date 28 Feb. 2011; clear liquid; Baxter supplied by TPS Medical)

Test and Reference Substance Storage
The test substance was refrigerated (2° C. to 8° C.) and the reference substance was stored frozen (approximately −20° C.).

Animals
Species: Mice (athymic)
Strain: CD-1 nu/nu
Sex: Female
Number of animals: 60 animals were allocated to study; 9 were transferred to another study and the remaining 31 animals were terminated by cervical dislocation
Age range: 6 to 8 weeks (based on the average body weight)
Weight range: 22 to 24 g
Acclimatisation: At least 3 days after delivery, prior to tumor implantation
Source: Charles River UK Ltd
Experimental Design
Formulation of the Test and Reference Substances
The test substance, BTX, was obtained as a lyophilised powder (50 units per vial) and was reconstituted prior to injection with 4.44 mL sterile saline. Once reconstituted, BTX was stored refrigerated at 2° C. to 8° C. until immediately prior to dosing and was used within 4 h. The resulting dosing solution was 11.26 units/mL and was administered as four 10 µL injections per mouse.

The reference substance, Paclitaxel, was supplied as a powder. This powder was dissolved in a minimal volume (50 µL) of DMSO, and formulated as a 0.5 mg/mL solution in 5% ethanol, 10% cremaphor, 85% sterile saline (0.9% w/v). Solutions were protected from light and used within approximately 30 min of preparation.

Group Sizes, Doses and Identification Numbers
There were 6 treatment groups with a target of 10 mice per group. One hundred mice were injected subcutaneously with $7\times10^6$ HCT-116 tumor cells to allow selection of optimal tumors for inclusion in the study. Prior to treatment, animals were ranked according to tumor volume. Tumors of the appropriate size were allocated to the various treatment groups using a method recommended by a statistician to give the best distribution of tumor sizes between groups.

Each group was given a number (1 to 6). The treatment groups comprised the following:
Group 1 Vehicle for BTX 4×10 μL
Group 2 BTX 4×0.112 Upper 10 μL
Group 3 Vehicle for Paclitaxel 10 mL/kg
Group 4 Paclitaxel 5 mg/kg
Group 5 Vehicle for BTX 4×10 μL
Vehicle for Paclitaxel 10 mL/kg
Group 6 BTX 4×0.112 U per 10 μL
Paclitaxel 5 mg/kg For BTX each treatment was administered in an injection volume of 10 μL. The vehicle for BTX was sterile saline (0.9% w/v). On Day 0, mice received four peri-tumoral doses of the test substance or vehicle on 1 occasion, at four distinct sites. At each site, the edge of the injection "bleb" was approximately 1 to 2 mm from the edge of the tumor ensuring that BTX was not injected into the tumor mass.

For Paclitaxel each treatment was administered in an injection volume of 10 mL/kg. The dose level was 5 mg/kg. This dose level established that 5 mg/kg resulted in a sub-maximal growth inhibitory response in a HCT116 xenograft model. The vehicle for Paclitaxel was an equivalent volume (50 μL) of DMSO in 5% ethanol, 10% cremaphor, 85% sterile saline (0.9% w/v). Mice received intravenous (tail vein) doses every 4 days on Days 5 (five days after BTX administration), 9, 13, 17, 21 and 25.

Body Weights

Animals were weighed regularly during the dosing period and at least twice weekly for the remainder of the study and body weights recorded.

Procedure

Human HCT116 colorectal tumor cells (American Type Culture Collection (ATCC), Maryland, USA) were harvested from sub-confluent cultures growing in vitro and the number of viable cells determined. Cells were re-suspended in sterile phosphate buffered saline at a concentration of approximately $7 \times 10^7$ cells/mL. Nude (nu/nu) athymic mice were injected subcutaneously in the right flank with approximately $7 \times 10^6$ cells in a volume of 0.1 mL.

Animals were examined regularly for the appearance of tumors.

Treatment commenced when the majority of the tumors were in the range 50 to 150 mm$^3$. The surplus implanted mice were either 'no takes' or had tumors that were too large, misshapen or unfit for selection.

Tumor dimensions were recorded (length and width), and tumor volumes calculated using the formula $(W^2 \times L)/2$, where W is the widest tumor dimension and L is the longest. When mice were killed due to tumor size, clinical condition, or at the termination of the study, the tumors (including approximately 2 cm of the surrounding tissue) were removed, then bisected (with the exception of the animals discussed in section 3.1). Half was frozen rapidly in liquid nitrogen, the other half was fixed in formalin. Tissue samples were sectioned at approximately 5 μm thickness, stained with haematoxylin and eosin and analysed by a veterinary pathologist. The tumor tissue was evaluated for central necrosis, mitotic rate, apoptosis and vascularisation; the surrounding tissue was evaluated for inflammatory change and vascularisation. A grade was given from 1 (lowest) to 5 (highest). Other changes were noted where appropriate including ulceration of overlying skin, decrease in thickness of tumor wall, necrosis and overall size.

Data Analysis

Calculations of relative tumor volumes and plots of tumor growth curves were performed. Tumor volume was calculated by the formula $(W^2 \times L)/2$, where W is the tumor measurement at the widest point, and L is the tumor dimension at the longest point. Relative tumor volume (RTV) was calculated for tumors using the tumor volume on the first day of treatment, Day 0, e.g. tumor volume on Day 3/tumor volume on Day 0 (V/V$_0$).

Tumor Growth Modelling

In order for statistical comparisons to be made between treatment groups, tumor growth modelling was performed using GraphPad Prism v5.02 and SAS v9.1.

Expected tumor volume (V) can be expressed in the following model:

$$V = V_0 \cdot e^{\lambda \cdot day}$$

Where $V_0$ is the tumor volume on Day 0 and $\lambda$ is the tumor growth rate.

This model implies that the natural logarithmic transformation of the relative tumor volume (V/V$_0$) can be expressed in terms of a linear regression with intercept of 0 and a slope of $\lambda$.

i.e. $\log(V/V_0) = \lambda \cdot day$

Natural logarithmic transformations were performed on individual animal relative tumor volumes and linear regression (forced though 0) was carried out on the data in order to calculate a linear regression slope parameter for each animal. The slope of each animal ($\lambda_i$) is equivalent to the rate of growth of relative tumor volume, on a log transformed scale.

Analysis of variance (ANOVA) modeling was performed on the individual animal slope estimates ($\lambda_i$), with treatment as the only effect. This provided estimates of the mean slope for each treatment.

Doubling time (DT) was then estimated for each treatment, using the formula:

$$DT_{treat} = (\log_e 2)/\lambda_{treat}$$

Where $\lambda_{treat}$ is the estimated mean linear regression slope for each treatment.

Statistical Analysis

In order to make statistical comparisons between tumor growth rates an analysis of covariance (ANCOVA) model was fitted to the individual animal slope estimates. The three vehicle groups were tested to establish if there was any statistical difference between them. There was no evidence of a statistical difference between the vehicles so this allowed the vehicle groups data to be combined and analyzed as a single group.

Doubling time and the confidence limits of doubling time were calculated by dividing $\log_e 2$ by the slope estimates (and 95% confidence limits) provided by the ANCOVA for each treatment. P-values for the difference between treatments estimated slopes were also calculated.

Assumptions of normality of residuals and equal variance were valid for these data.

Comparisons were made between each treatment group and the combined vehicle group.

Growth delay calculations were performed by subtracting the doubling time each treatment group from the doubling time of the combined vehicle groups. Specific growth delay calculations were performed by dividing the growth delay obtained (in days) by the tumor doubling time of the combined vehicle groups.

Results

The treatment regimen for BTX was not well tolerated in approximately half of the animals treated. It would appear that the tolerance of BTX varies greatly between individual mice.

Signs of toxicity (hunched posture, prominent spines and rib cages, unsteadiness and weight loss of up to 18.6%) were observed on Days 3 and 4 of the study and 11 mice were terminated as a result (6 in Group 2, BTX and 5 in Group 6, BTX+Paclitaxel). Several mice were terminated from Day 28 onwards due to a tumor size of >1500 $mm^3$.

No substantial difference in mean tumor size was observed between the treatment groups on Day 0, the day of ranking. Mean start volumes for each group are shown in Table 1. The mean tumor volumes for each measurement day are presented in Table 2, while the mean relative tumor volumes for each measurement day are presented in Table 3 and shown graphically in FIG. 1. Modeling the growth of individual tumors is shown graphically in FIG. 2. The estimated doubling times calculated using the group mean slope parameters, 95% confidence limits and p-values are presented in Table 4. Growth (doubling time) delay and specific growth delays due to administration of test and reference substances are presented in Table 5.

TABLE 1

Mean tumour volumes following allocation to treatment groups

| Group | Treatment | Mean (±s.e.m.) tumour volume ($mm^3$) | n |
|---|---|---|---|
| 1 | Vehicle for BTX* | 101.7 ± 9.7 | 10 |
| 2 | BTX | 101.2 ± 9.4 | 10 |
| 3 | Vehicle for Paclitaxel# | 100.6 ± 9.7 | 10 |
| 4 | Paclitaxel | 100.0 ± 9.9 | 10 |
| 5 | Vehicle for BTX* + Vehicle for Paclitaxel# | 100.7 ± 10.2 | 10 |
| 6 | BTX + Paclitaxel | 100.8 ± 10.3 | 10 |

*0.9% w/v sterile saline.
DMSO in 5% ethanol, 10% cremaphor, 85% sterile saline (0.9% w/v).

TABLE 2

Mean tumour volume of HCT-116 human colorectal cancer tumour xenografts in nude mice following treatment with Botulinum Toxin A. Paclitaxel, Botulinum Toxin A + Paclitaxel or the corresponding vehicle groups

| | | Mean tumour volume ($mm^3$) ± s.e.m. on Day: | | | | | | |
|---|---|---|---|---|---|---|---|---|
| Group | Treatment | 0 | 5 | 7 | 11 | 14 | 18 | 20 |
| 1 | Vehicle for BTX* | 101.7 ± 9.7 | 194.5 ± 27.2 | 250.2 ± 32.9 | 304.5 ± 43.5 | 398.4 ± 56.7 | 483.0 ± 76.7 | 523.2 ± 121.7 (9) |
| 2 | BTX | 101.2 ± 9.4 | 96.7 ± 22.5 (4) | 135.3 ± 32.5 (4) | 172.0 ± 25.4 (4) | 203.9 ± 36.1 (4) | 250.8 ± 48.8 (4) | 245.1 ± 62.1 (4) |
| 3 | Vehicle for Paclitaxel# | 100.6 ± 9.7 | 164.7 ± 17.7 | 206.6 ± 23.2 | 266.6 ± 35.4 | 351.7 ± 49.9 | 406.5 ± 52.3 | 448.5 ± 65.3 |
| 4 | Paclitaxel | 100.0 ± 9.9 | 175.1 ± 21.9 | 218.9 ± 27.4 | 245.2 ± 38.9 | 306.1 ± 49.3 | 407.4 ± 74.3 | 437.6 ± 79.4 |
| 5 | Vehicle for BTX* + Vehicle for Paclitaxel# | 100.7 ± 10.2 | 140.4 ± 13.0 | 183.6 ± 28.1 | 241.1 ± 38.4 | 294.3 ± 42.3 | 373.6 ± 54.2 | 455.8 ± 95.7 |
| 6 | BTX + Paclitaxel | 100.8 ± 10.3 | 125.3 ± 14.4 (5) | 141.0 ± 22.7 (5) | 180.6 ± 42.5 (5) | 231.1 ± 48.6 (5) | 262.0 ± 56.4 (5) | 256.1 ± 70.7 (5) |

*0.9% w/v sterile saline.
DMSO in 5% ethanol, 10% cremaphor, 85% sterile saline (0.9% w/v).
n = 10 unless otherwise stated in parenthesis.

TABLE 3

Mean relative tumour volume of HCT-116 human colorectal cancer tumour xenografts in nude mice following treatment with Botulinum Toxin A, Paclitaxel, Botulinum Toxin A + Paclitaxel or the corresponding vehicle groups

| | | Mean relative tumour volume ± s.e.m. on Day: | | | | | | |
|---|---|---|---|---|---|---|---|---|
| Group | Treatment | 0 | 5 | 7 | 11 | 14 | 18 | 20 |
| 1 | Vehicle for BTX* | 1.0 ± 0.0 | 2.0 ± 0.3 | 2.5 ± 0.4 | 3.1 ± 0.5 | 4.0 ± 0.6 | 4.9 ± 0.9 | 4.9 ± 1.3 (9) |
| 2 | BTX | 1.0 ± 0.0 | 1.0 ± 0.2 (4) | 1.5 ± 0.3 (4) | 2.0 ± 0.2 (4) | 2.3 ± 0.2 (4) | 2.8 ± 0.3 (4) | 2.6 ± 0.6 (4) |
| 3 | Vehicle for Paclitaxel# | 1.0 ± 0.0 | 1.8 ± 0.3 | 2.3 ± 0.4 | 3.0 ± 0.6 | 3.9 ± 0.9 | 4.6 ± 1.0 | 4.9 ± 1.0 |
| 4 | Paclitaxel | 1.0 ± 0.0 | 1.7 ± 0.1 | 2.2 ± 0.1 | 2.4 ± 0.2 | 3.0 ± 0.3 | 4.1 ± 0.5 | 4.4 ± 0.6 |
| 5 | Vehicle for BTX* + Vehicle for Paclitaxel# | 1.0 ± 0.0 | 1.6 ± 0.4 | 2.2 ± 0.7 | 3.0 ± 1.0 | 3.6 ± 1.1 | 4.6 ± 1.5 | 5.8 ± 2.1 |
| 6 | BTX + Paclitaxel | 1.0 ± 0.0 | 1.2 ± 0.1 (5) | 1.4 ± 0.2 (5) | 1.7 ± 0.3 (5) | 2.2 ± 0.3 (5) | 2.5 ± 0.4 (5) | 2.4 ± 0.5 (5) |

*0.9% w/v sterile saline.
DMSO in 5% ethanol, 10% cremaphor, 85% sterile saline (0.9% w/v).
n = 10 unless otherwise stated in parenthesis.

TABLE 4

Estimated doubling times of the human colorectal tumour xenograft, HCT116, following treatment with Botulinum Toxin A, Paclitaxel, Botulinum Toxin A + Paclitaxel or the corresponding vehicle groups

| Group | Treatment | Doubling time (Days) | Lower 95% CI | Upper 95% CI | P-value (treatment compared with vehicle) |
|---|---|---|---|---|---|
| 1, 3, 5 | Vehicle | 9.7 | 8.5 | 11.4 | — |
| 2 | BTX | 12.5 | 8.3 | 25.8 | 0.29 |
| 4 | Paclitaxel | 10.5 | 8.2 | 14.4 | 0.63 |
| 6 | BTX + Paclitaxel | 16.3 | 10.2 | 40.8 | 0.04* |

*p = <0.05.

TABLE 5

Growth delay of the human colorectal tumour xenograft, HCT116, following treatment with Botulinum Toxin A, Paclitaxel, Botulinum Toxin A + Paclitaxel or the corresponding vehicle groups

| Group | Treatment | Estimated doubling time (Days) | Growth delay (Days delay per control doubling) | Specific growth delay |
|---|---|---|---|---|
| 1, 3, 5 | Vehicle | 9.7 | — | — |
| 2 | BTX | 12.5 | 2.8 | 0.29 |
| 4 | Paclitaxel | 10.5 | 0.8 | 0.08 |
| 6 | BTX + Paclitaxel | 16.3 | 6.6 | 0.68 |

Over the 42 day measurement period, the estimated doubling time of the combined control groups was 9.7 days (lower 95% confidence limit 8.5, upper 95% confidence limit 11.4), for the BTX group the doubling time was 12.5 days (lower 95% confidence limit 8.3, upper 95% confidence limit 25.8), for Paclitaxel group the doubling time was 10.5 days (lower 95% confidence limit 8.2, upper 95% confidence limit 14.4) and for the BTX+Paclitaxel combination treatment group the doubling time was 16.3 days (lower 95% confidence limit 10.2, upper 95% confidence limit 40.8). The reduction of tumor growth rate compared to vehicle in the BTX+Paclitaxel combination treatment group was statistically significant (p<0.05, ANCOVA). The differences in growth rate between vehicle and the groups receiving Paclitaxel or BTX as single agents was not statistically significant.

Compared to the vehicle group, administration of BTX+Paclitaxel as a combination treatment, caused an estimated tumor doubling time delay of 6.6 days, which translated into a specific growth delay of 0.68. Administration of Paclitaxel as a single agent, caused an estimated tumor doubling time delay of 0.8 days, which translated into a specific growth delay of 0.08. Administration of BTX as a single agent, caused an estimated tumor doubling time delay of 2.8 days, which translated into a specific growth delay of 0.29.

The mean relative tumor volumes of mice receiving BTX+Paclitaxel as a combined treatment were lower than BTX vehicle treated mice until Day 34. The mean relative tumor volumes of mice receiving BTX as a single agent were lower than BTX vehicle treated mice throughout the study until Day 34. The mean relative tumor volumes of mice receiving Paclitaxel as a single agent were lower than Paclitaxel vehicle treated mice the study until Day 34 (FIG. 1 and Table 3).

Histological analysis of excised tumors showed central necrosis of varying degrees with a high mitotic rate and low grade apoptosis. There was little variation in vascularization within the tumors and a degree of inflammation in the tissue surrounding the tumor was present usually spread all round the subcutis with a blood supply in this tissue as expected. Where ulceration of the skin occurred there was an increase in inflammatory change as would be expected.

The groups given BTX had fewer animals for evaluation thus any interpretation of group trends was difficult.

Group 2 BTX (4 animals) showed a reduction in thickness of the tumor in 3/4 animals and generally there was an increased inflammatory response in the surrounding tissue.

Group 4 Paclitaxel (10 animals) generally showed a reduction in thickness of the tumor in 5/10 animals, mainly Grade 2, with an increase in fibrosis of the tumor in 3 animals. Group 3 (vehicle for Paclitaxel) showed a reduction in tumor thickness in 3/10 animals at Grade 1 but in all these animals there was ulceration of the skin overlying the tumor. Otherwise this group was similar to the other 2 vehicle only groups (Groups 1 and 5).

Group 6 BTX+Paclitaxel (5 animals) 2/5 had small tumors with another 1/5 showing a small reduction in tumor thickness. There was ulceration of the skin in one animal.

In nude athymic mice bearing subcutaneous human colorectal tumor HCT116 xenografts, treatment with Paclitaxel at 5 mg/kg i.v. in combination with BTX, 0.45 units/mouse, subcutaneous (peri-tumoral) resulted in a statistically significant reduction in estimated tumor growth rate and a reduction in relative tumor volume compared to control throughout the study duration.

Treatment with a sub-maximal dose of reference substance as a single agent, Paclitaxel (5 mg/kg i.v.), marginally reduced the estimated tumor growth rate in a manner consistent with its recognised anti-tumor activity at higher doses although these data were not statistically significant. A reduction of relative tumor volume compared to control was seen for the majority of the study duration.

Treatment with the test substance as a single agent, BTX (0.45 units/mouse, subcutaneous, peri-tumoral), reduced the estimated tumor growth rate although these data were not statistically significant. A reduction of relative tumor volume compared to control was seen for the majority of the study duration.

Due to clinical signs in the two BTX treated groups (Groups 2 and 6) early in the study the n numbers were reduced and therefore the statistical power of the study was reduced.

Administration of BTX appeared to cause an increase in inflammation and a decrease in tumor thickness. Administration of Paclitaxel showed a trend towards a decrease in tumor thickness and an increase in fibrosis. Administration of both in combination produced a reduction in tumor size or thickness in more than half of the animals.

It can be seen that from these data Botulinum Toxin A (BTX) may potentiate the efficacy of a sub-maximal dose level of the anti-cancer drug Paclitaxel against the human colorectal cancer xenograft HCT-116 in nude mice.

Example #15

Cancer Suspected on Radiographs

A 47 year old patient is found to have a 30 mm mass in the colon on CT scan images obtained for abdominal pain. The suspicion is high that the lesion represents a mucosal cancer. During colonoscopy, frozen section biopsy confirms cancer. The lesion's borders are identified. BOTOX® is injected into the submucosal region in 6 separate injections around the cancer. A total of 60 units are given. The injections are placed into the non-cancerous tissue surrounding the cancer. Injections are made about 10 mm away from the edge of the cancer. The patient then undergoes chemotherapy.

Example #16

Cancer Suspected and Confirmed During Colonoscopy

A 47 year old patient is found to have a 30 mm mass in the colon during colonoscopy. The suspicion is high that the lesion represents a mucosal cancer. During colonoscopy, frozen section biopsy confirms cancer. The lesion's borders are identified. BOTOX® is injected into the submucosal region in 6 separate injections around the cancer. A total of 60 units are given. The injections are placed into the non-cancerous tissue surrounding the cancer. Injections are made about 10 mm away from the edge of the cancer. The patient then undergoes radiation therapy.

Example #17

Cancer Suspected and Botox® is Administered Around the Periphery of the Cancer (Before Confirmation of Cancer) During Colonoscopy A 47 year old patient is found to have a 30 mm mass in the colon during colonoscopy. The suspicion is high that the lesion represents a mucosal cancer. Biopsy is sent. The lesion's borders are identified. Six separate injections of BOTOX® are administered into the submucosal region away from the cancer. A total of 60 units (i.e., 6 injections×10 units per injection) is given. The injections are placed into the non-cancerous tissue, about 10 mm away from the edge of the cancer. The patient then undergoes chemotherapy.

Example #18

Cancer Suspected, Confirmed, then Patient Brought Back for Repeat Colonoscopy

A 47 year old patient is found to have a 30 mm mass in the colon during colonoscopy. The suspicion is high that the lesion represents a mucosal cancer. Biopsy is sent. Final biopsy 3 days later confirms cancer. The patient is prepped for repeat colonoscopy. The lesion is identified and its borders are identified. BOTOX® is injected into the submucosal region in 6 separate injections around the cancer. A total of 60 units is given. The injections are placed into the non-cancerous tissue surrounding the cancer. Injections are made about 10 mm away from the edge of the cancer. The patient then undergoes chemotherapy.

As noted above, Botulinum toxin is available from multiple sources. In addition, it is available from Allergan as Botox®, a BTX-A formulation; DySport®, another BTX-A preparation available in Europe from Ipsen, Ltd; and Myobloc® (or NeuroBloc® in Europe), a BTX-B preparation available from Elan Pharmaceuticals.

Botulinum for use in the present invention can also be made by known pharmaceutical techniques by, for example, dissolving pharmaceutically acceptable Botulinum toxin in a pharmaceutically acceptable carrier useful for injection, such that the Botulinum is dissolved to the desired strength or concentration. These preparations can be made fresh or premade. Other pharmaceutically acceptable ingredients, such as preservatives, can be added. These preparations are made by techniques known in the art.

The amount of Botulinum toxin to use varies, of course, according to the size of the tumor to be treated. The maximum dosage of Botulinum A to administer should not exceed 500 units per injection session. Preferably, 0.01-100 units of Botulinum A should be used. More preferably, the dosage of Botulinum A should be in the range of from about 1 unit to about 50 units. Even more preferably, the dosage of Botulinum A should be in the range of from about 5 units to about 40 units.

It is known that an electric current can enhance the absorption of botulinum toxin into tissues. Black, et al., 1:Cell Biol-1986 August; 103(2): 535-44; Hesse.sub.1 et al., 1: Neurosci Lett. 1995 Dec. 1; 201(1) 37-40; Hesse, et al., 1: Clin. Rehabil. 1998 October; 12(5): 381-8.

Accordingly, one embodiment of the present invention is to apply an electric current to or around the area to be treated. This should decrease the amount of botulinum toxin needed for effective results.

If a different neurotoxin is used, such as Botulinum B, C, D, E F or G, the dosage should conform to the above dosage for Botulinum A. Conversions, known in the art, can be used to calculate these dosages.

* * *

Having thus described in detail embodiments of the present invention, it is to be understood that the invention defined by the above paragraphs is not to be limited to particular details set forth in the above description as many apparent variations thereof are possible without departing from the spirit or scope of the present invention.

Each patent, patent application, and publication cited or described in the present application is hereby incorporated by reference in its entirety as if each individual patent, patent application, or publication was specifically and individually indicated to be incorporated by reference.

What is claimed is:

1. A method of weakening or paralyzing the muscle fibers surrounding a neoplasm in a patient, comprising applying to the non-cancerous area around said neoplasm a therapeutically effective amount of botulinum toxin in combination with an anti-cancer drug or anti-cancer therapy, such that the therapeutically effective amount of the botulinum toxin reduces the spread of cells from the neoplasm, thereby inhibiting the growth or metastases of the neoplasm.

2. The method of claim 1, wherein the botulinum toxin is administered before the anti-cancer drug or anti-cancer therapy is administered.

3. The method of claim 1, wherein the botulinum toxin-neurotoxin is administered together with the anti-cancer drug or anti-cancer therapy.

4. The method of claim 2 or claim 3, wherein the anti-cancer drug is selected from the group consisting of: an alkylating agent, an antimetabolite, an anthracycline, mitoxantrone, topoisomerase, a mitotic inhibitor, a steroid, a differentiation agent, a hormone, and an immunotherapy agent.

5. The method of claim 4, wherein the mitotic inhibitor is selected from the group consisting of a taxane, an epothilone, and a vinca alkaloid.

6. The method of claim 5, wherein the taxane is paclitaxel or docetaxel.

7. The method of claim 6, wherein the taxane is paclitaxel.

8. The method of claim 1, wherein the botulinum toxin denervates muscle tissue surrounding the neoplasm.

9. The method of claim 1, wherein the botulinum toxin is botulinum toxin type A or botulinum toxin type B.

* * * * *